United States Patent
Watanabe

(10) Patent No.: US 12,355,126 B2
(45) Date of Patent: Jul. 8, 2025

(54) ELASTICALLY CONFIGURED WAVEGUIDE CONNECTING STRUCTURE USABLE IN A WAVEGUIDE CONNECTOR, A WAVEGUIDE UNIT, A MODE CONVERTER, AN IMAGING DEVICE AND AN ENDOSCOPE

(71) Applicant: OLYMPUS CORPORATION, Hachioji (JP)

(72) Inventor: Tadashi Watanabe, Nagano (JP)

(73) Assignee: OLYMPUS CORPORATION, Tokyo (JP)

( * ) Notice: Subject to any disclaimer, the term of this patent is extended or adjusted under 35 U.S.C. 154(b) by 614 days.

(21) Appl. No.: 17/683,626

(22) Filed: Mar. 1, 2022

(65) Prior Publication Data

US 2022/0190458 A1 Jun. 16, 2022

Related U.S. Application Data

(63) Continuation-in-part of application No. PCT/JP2020/038520, filed on Oct. 12, 2020.

(51) Int. Cl.
*H01P 1/04* (2006.01)
*A61B 1/00* (2006.01)
(Continued)

(52) U.S. Cl.
CPC .......... *H01P 1/042* (2013.01); *A61B 1/00126* (2013.01); *H01P 3/122* (2013.01);
(Continued)

(58) Field of Classification Search
CPC ........... H01P 3/122; H01P 1/042; H01P 5/024
(Continued)

(56) References Cited

U.S. PATENT DOCUMENTS 12,046,793 B2 * 7/2024 Watanabe et al. ...... H01P 3/122
2003/0030503 A1 2/2003 Paynter et al.
(Continued)

FOREIGN PATENT DOCUMENTS

CN 104285340 A 1/2015
JP S54146144 U 10/1979
(Continued)

OTHER PUBLICATIONS

Japanese Office Action dated May 14, 2024 (and English translation thereof), issued in counterpart Japanese Application No. 2022-513452.
(Continued)

*Primary Examiner* — Benny T Lee
(74) *Attorney, Agent, or Firm* — Holtz, Holtz & Volek PC

(57) ABSTRACT

Provided is a waveguide connecting structure of connecting a first waveguide to a second waveguide, or to a transmitting and receiving device. The waveguide connecting structure included: an elastic body configured to cause an external conductor to closely contact a dielectric body, the external conductor and the dielectric body being included in the first waveguide, the external conductor covering an outer periphery of the dielectric body; and a three-dimensional body configured to hold the dielectric body, and the second waveguide or the transmitting and receiving device, the three-dimensional body having electric conductivity inside an insertion hole holding the first waveguide, and the external conductor of the first waveguide including a radially spread portion that has been radially spread, the radially spread portion being where the first waveguide and the three-dimensional body are connected to each other.

18 Claims, 31 Drawing Sheets

(51) Int. Cl.
  *H01P 3/12* (2006.01)
  *H01P 5/02* (2006.01)
  *H04N 23/50* (2023.01)
  *A61B 1/04* (2006.01)

(52) U.S. Cl.
  CPC .............. *H01P 5/024* (2013.01); *H01P 5/026* (2013.01); *H04N 23/50* (2023.01); *A61B 1/00009* (2013.01); *A61B 1/04* (2013.01); *H04N 23/555* (2023.01)

(58) Field of Classification Search
  USPC ........................................ 333/24 R, 248, 254
  See application file for complete search history.

(56) References Cited

U.S. PATENT DOCUMENTS

| | | |
|---|---|---|
| 2011/0047588 A1 | 2/2011 | Takeuchi et al. |
| 2015/0107896 A1 | 4/2015 | Kato et al. |
| 2016/0056860 A1 | 2/2016 | Okada |
| 2016/0126611 A1 | 5/2016 | Erskine et al. |
| 2018/0136456 A1 | 5/2018 | Watanabe et al. |
| 2022/0285815 A1 | 9/2022 | Watanabe et al. |

FOREIGN PATENT DOCUMENTS

| | | |
|---|---|---|
| JP | S60006302 U | 1/1985 |
| JP | H08195605 A | 7/1996 |
| JP | 2003110313 A | 4/2003 |
| JP | 2008193481 A | 8/2008 |
| JP | 2011044953 A | 3/2011 |
| JP | 2017147548 A | 8/2017 |
| JP | 2017147551 A | 8/2017 |
| JP | 6343827 B2 | 6/2018 |
| JP | 2020058524 A | 4/2020 |
| JP | 2021103819 A | 7/2021 |
| WO | 2014162833 A1 | 10/2014 |
| WO | 2017002585 A1 | 1/2017 |
| WO | 2021131224 A1 | 7/2021 |

OTHER PUBLICATIONS

International Search Report (ISR) dated Dec. 22, 2020, issued in International Application No. PCT/JP2020/038520.

Written Opinion dated Dec. 22, 2020, issued in International Application No. PCT/JP2020/038520.

Chinese Office Action (and an English language translation thereof) dated Mar. 4, 2024, issued in counterpart Chinese Application No. 202080059105.8.

\* cited by examiner

ELASTICALLY CONFIGURED WAVEGUIDE CONNECTING STRUCTURE USABLE IN A WAVEGUIDE CONNECTOR, A WAVEGUIDE UNIT, A MODE CONVERTER, AN IMAGING DEVICE AND AN ENDOSCOPE

CROSS-REFERENCE TO RELATED APPLICATION

This application is a continuation-in-part of International Application No. PCT/JP2020/038520, filed on Oct. 12, 2020, the entire contents of which are incorporated herein by reference.

BACKGROUND

1. Technical Field

The present disclosure relates to waveguide connecting structures, waveguide connectors, waveguide units, mode converters, imaging devices, and endoscopes, and particularly relates to waveguide connecting structures, waveguide connectors, waveguide units, mode converters, imaging devices, and endoscopes, in which the waveguides have braided external conductors.

2. Related Art

Starting in the broadcasting sector, efforts to increase resolution of images represented by 4K and 8K images are being made in recent years. Images having high resolutions, like 4K or 8K images, have large volumes of image information due to their large numbers of pixels, and communication speeds on the order of several tens of gigabits per second are needed for these images.

However, it is difficult for a transmission system using a metallic line, which is often conventionally adopted for short distance information transmission, to be compatible with a communication speed of about several tens of gigabits per second. Specific examples of conventional transmission systems include a coaxial line, a twisted pair line, or a twinaxial line.

Conventional optical communication technology adopted in long distance transmission or high speed communication at data centers may be used for transmission of large volumes of information exemplified by high resolution images. However, transmitting and receiving units for optical communication are very expensive and are difficult to be adopted for communication over short distances. Furthermore, because optical communication requires high accuracy on the order of several micrometers for connection between lines and can be disconnected because of fine dust attached on a connected surface, optical communication may not be reliable for repetitive connection. This means that optical communication technology has been unsuitable as a substitute for transmission systems using metallic lines adopted in conventional short distance communication.

Under the above-described circumstances, communication systems using waveguides that are able to transmit millimeter radio waves are being developed as wired communication means that enable high speed communication on the order of several tens of gigabits per second or more. Such communication systems can thus achieve inexpensiveness and connection reliability, all at high levels. For example, Japanese Patent Application Laid-open No. 2017-147548 discloses a waveguide including a hollow cylindrical dielectric body and a cylindrical conductor arranged outside the hollow cylindrical dielectric body. Furthermore, International Publication No. WO 2014/162833 discloses a waveguide including: a dielectric body arranged inside the waveguide; a metallic plated layer covering two faces where an electric field intersects; and a protective layer covering around the dielectric body having the two faces covered by the metallic plated layer. Similarly, Japanese Patent No. 6343827 discloses a waveguide including: a linear dielectric body arranged at the center of the waveguide; and an external conductor made of a braided flat foil structure.

SUMMARY OF THE INVENTION

In some embodiments, provided is waveguide connecting structure of connecting a first waveguide to a second waveguide, or to a transmitting and receiving device. The waveguide connecting structure includes: an elastic body configured to cause an external conductor to closely contact a dielectric body, the external conductor and the dielectric body being included in the first waveguide configured to transmit radio waves having a frequency of millimeter waves or higher, the external conductor covering an outer periphery of the dielectric body; and a three-dimensional body configured to hold the dielectric body of the first waveguide, and the second waveguide or the transmitting and receiving device, the second waveguide being different from the first waveguide, the transmitting and receiving device being configured to transmit and receives radio waves, the three-dimensional body having electric conductivity inside an insertion hole holding the first waveguide, and the external conductor of the first waveguide including a radially spread portion that has been radially spread, the radially spread portion being where the first waveguide and the three-dimensional body are connected to each other.

In some embodiments, a waveguide connector includes: two or more of waveguide connecting structures where each is the waveguide connecting structure.

In some embodiments, a waveguide connector includes the waveguide connecting structure, the waveguide connector connecting the first waveguide and a hollow waveguide to each other, the hollow waveguide being positioned on one side of the three-dimensional body, the one side being opposite to another side of the three-dimensional body, the other side being where the fixing body is positioned.

In some embodiments, a waveguide unit includes: the waveguide connecting structure, the fixing body being provided each at both ends of the first waveguide.

In some embodiments, a mode converter includes: the waveguide connecting structure for connecting the first waveguide and the transmitting and receiving device to each other, the transmitting and receiving device including an antenna for mode conversion between a mode for electromagnetic waves and a mode for electric signals.

In some embodiments, an imaging device includes: the waveguide connecting structure; an optical lens configured to condense incident light; an imaging element configured to photoelectrically convert the light condensed by the optical lens; and an image processor configured to process a signal input from the imaging element via the waveguide.

In some embodiments, an endoscope includes: the imaging device.

The above and other features, advantages and technical and industrial significance of this disclosure will be better understood by reading the following detailed description of presently preferred embodiments of the disclosure, when considered in connection with the accompanying drawings.

DETAILED DESCRIPTION OF THE INVENTION

Modes, hereinafter referred to as "embodiments", for implementing the disclosure will be described below by reference to the drawings. The disclosure is not limited by the embodiments described below. Furthermore, any portions that are the same will be assigned with the same reference sign, throughout the drawings and the detailed description of the drawings.

First Embodiment

Figure 1:
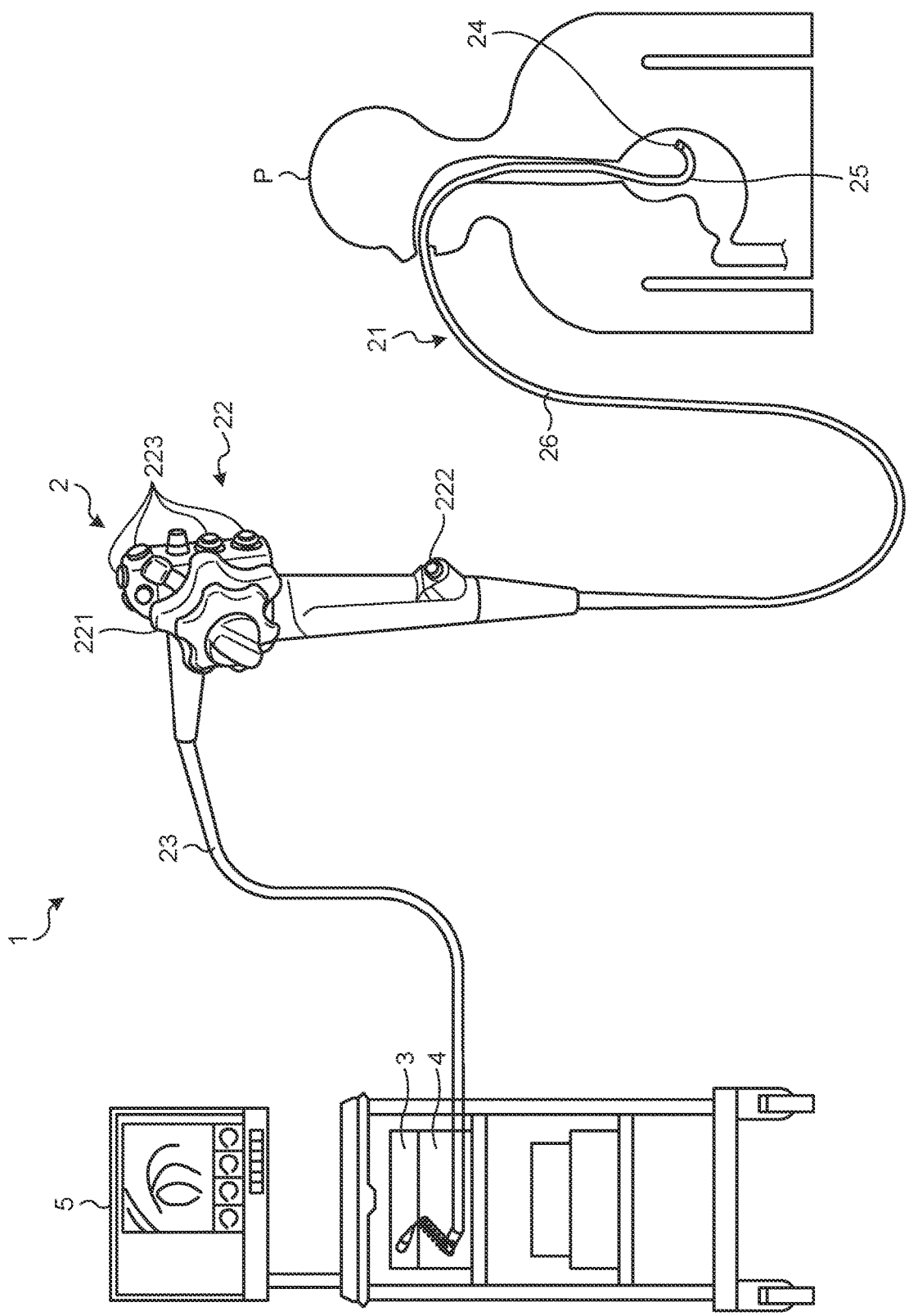
FIG. 1 is a diagram schematically illustrating an endoscope system according to a first embodiment of the disclosure.
Figure 2:
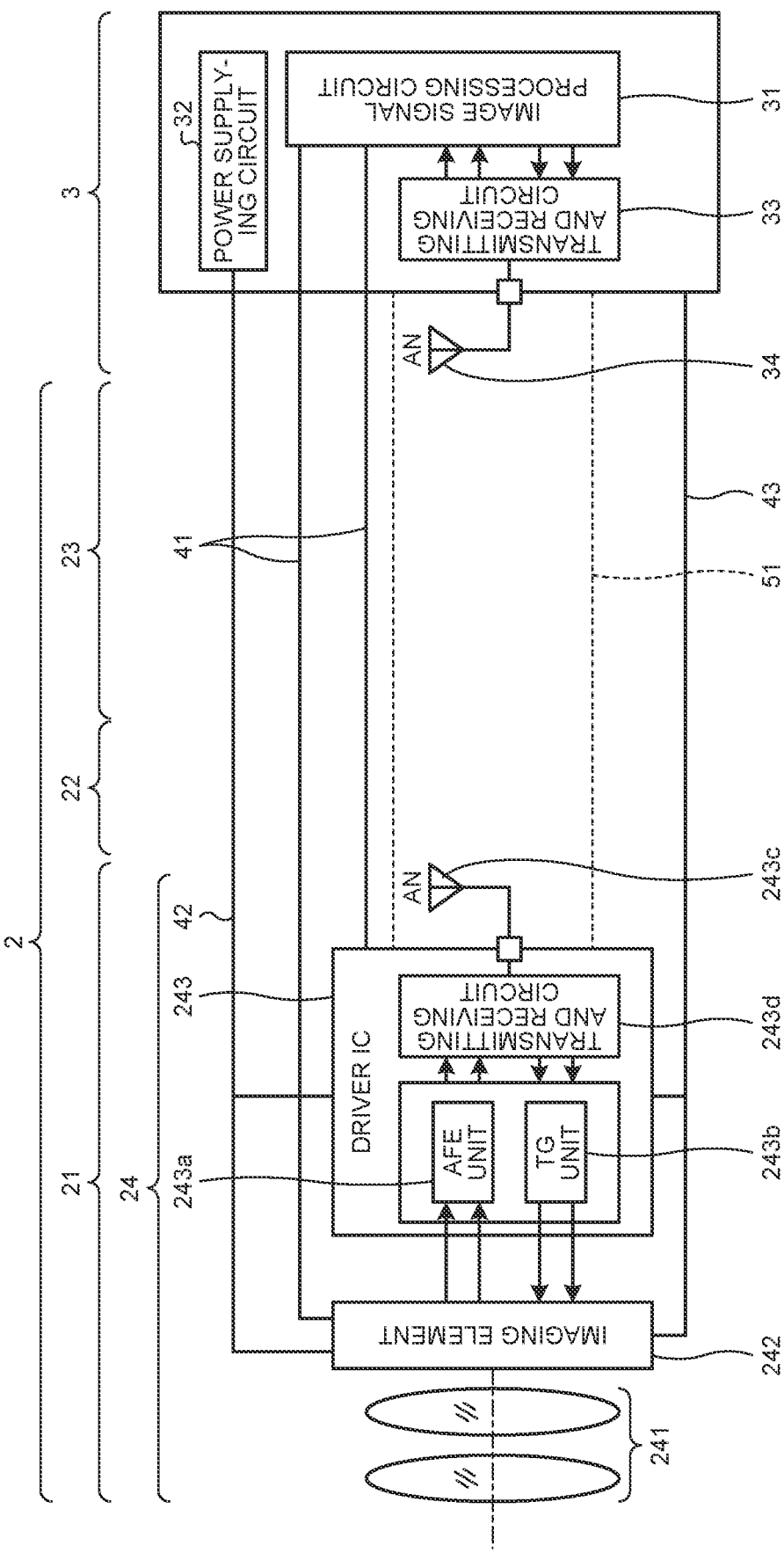
FIG. 2 is a block diagram illustrating a schematic configuration of the endoscope system according to the first embodiment of the disclosure.

FIG. 1 is a diagram illustrating a schematic configuration of an endoscope system according to a first embodiment of the disclosure. FIG. 2 is a block diagram illustrating a schematic configuration of the endoscope system according to the first embodiment.

An endoscope system 1 illustrated in FIG. 1 and FIG. 2 includes: an endoscope 2 that captures an in-vivo image of a subject by insertion of a distal end portion of the endoscope 2 into the subject; a processing device 3 that executes predetermined signal processing on an imaging signal captured by the endoscope 2 and integrally controls the overall operation of the endoscope system 1; a light source device 4 that generates illumination light to be emitted from a distal end of the endoscope 2; and a display device 5 that displays the in-vivo image generated through the signal processing by the processing device 3.

The endoscope 2 includes: an insertion unit 21 that has flexibility and is elongated; an operating unit 22 that is connected to a proximal end of the insertion unit 21 and receives input of various operation signals; and a universal cord 23 that extends in a direction different from a direction in which the insertion unit 21 extends from the operating unit 22, the universal cord 23 including various cables built therein for connection to the light source device 4 and the processing device 3.

The insertion unit 21 includes: a distal end portion 24 including an imaging element 244 built therein, the imaging element 244 including two-dimensionally arrayed pixels that generate a signal by receiving and photoelectrically converting light; a bending portion 25 that is formed of plural bending pieces and is freely bendable; and a flexible tube portion 26 that is connected to a proximal end of the bending portion 25, has flexibility, and is elongated. The insertion unit 21 is inserted into a body cavity of the subject, and captures, through an imaging element 242, an image of an object, such as tissue of a living body, the tissue being at a position where external light is unable to reach.

The distal end portion 24 includes: an optical system 241 for condensing light; and the imaging element 242 (an imaging unit) that receives the light condensed by the optical system 241, photoelectrically converts the received light into an electric signal, and executes predetermined signal processing on the electric signal.

The optical system 241 is formed using one or plural lenses, and has: an optical zooming function for changing the angle of view; and a focusing function for changing the focus.

The imaging element 242 photoelectrically converts light from the optical system 241 to generate image data. The imaging element 242 is implemented using, for example, a charge coupled device (CCD) image sensor, or a complementary metal oxide semiconductor (CMOS) image sensor.

The endoscope 2 includes a memory (not illustrated in the drawings) that stores: an execution program and a control program, for the imaging element 242 to execute various operations; and data including identification information of the endoscope 2. The identification information includes, for example, unique information (ID), the model year, specification information, and the transmission scheme, of the endoscope 2. Furthermore, the memory may temporarily store image data generated by the imaging element 242, for example.

The operating unit 22 includes: a bending knob 221 that bends the bending portion 25 upward, downward, leftward, and rightward; a treatment tool insertion portion 222 through which a treatment tool, such as biopsy forceps, an electric knife, or an examination probe, is inserted into the body cavity of the subject; and plural switches 223 serving as an operation input unit through which operation instruction signals are input, the operation instruction signals being for a gas feeding means, a water feeding means, and a peripheral device for screen display control, for example, in addition to the processing device 3. The treatment tool inserted from the treatment tool insertion portion 222 comes out from an opening (not illustrated in the drawings) via a treatment tool channel (not illustrated in the drawings) of the distal end portion 24.

The universal cord 23 includes, built therein, at least: a light guide that guides light emitted by the light source device 4; and an assembly cable including one or plural signal lines assembled together. The universal cord 23 is branched at an end portion of the universal cord 23, the end portion being opposite to that connected to the operating unit 22. A connector that is attachable to and detachable from the processing device 3, and a connector that is attachable to and detachable from the light source device 4 are provided at branched end portions of the universal cord 23. The universal cord 23 propagates illumination light emitted from the light source device 4, to the operating unit 22. Furthermore, the universal cord 23 transmits an image signal captured by the imaging element 242 provided in the distal end portion 24, to the processing device 3. The assembly cable includes: a signal line 41 for transmitting and receiving a drive signal for driving the imaging element 242 and information including the unique information related to the endoscope 2 (the imaging element 242); and a waveguide 51 for transmitting an image signal including image data. In this first embodiment, an electric signal is described as being transmitted by using a signal line, but an optical signal may be transmitted, or a signal may be transmitted between the endoscope 2 and the processing device 3 via wireless communication.

A driver IC 243 includes: an analog front-end (AFE) unit 243a that executes noise reduction and A/D conversion on an electric signal output by the imaging element 242; a timing generator (TG) unit 243b that generates drive timing of the imaging element 242 and pulses for various types of signal processing in the AFE unit 243a, for example; and a transmitting and receiving circuit 243d to which a transmitting and receiving antenna 243c is connected and which is for transmitting and receiving a digital signal to and from an image signal processing circuit 31 in the processing device 3 via the waveguide (a waveguide) 51, the digital signal having been output by the AFE unit 243a. The driver IC 243 is controlled by a control unit that controls operation of each unit of the driver IC 243 and operation of the imaging element 242. This control unit may be provided in the distal end portion 24 or the processing device 3.

The transmitting and receiving circuit 243*d* is a millimeter and submillimeter wave communication circuit formed of a so-called monolithic microwave integrated circuit (MMIC).

Furthermore, circuits, such as the AFE unit 243*a*, the TG unit 243*b*, and the transmitting and receiving circuit 243*d* in the driver IC 243 according to this embodiment are all manufactured by a silicon CMOS process.

Furthermore, the imaging element 242 and the driver IC 243 are connected to each other via, for example, a ceramic substrate, and plural passive components including a capacitor are mounted on the ceramic substrate.

A configuration of the processing device 3 will be described by reference to FIG. 2. The processing device 3 includes the image signal processing circuit 31, a power supplying circuit 32, and a transmitting and receiving circuit 33.

The image signal processing circuit 31 receives, from the endoscope 2, image data of illumination light for each color captured by the imaging element 242. When the image signal processing circuit 31 receives analog image data from the endoscope 2, the image signal processing circuit 31 generates a digital imaging signal by executing A/D conversion. Furthermore, when the image signal processing circuit 31 receives image data as an optical signal, from the endoscope 2, the image signal processing circuit 31 generates digital image data by executing photoelectric conversion.

The image signal processing circuit 31 generates an image by executing predetermined image processing on image data received from the endoscope 2 and outputs the image to the display device 5. This predetermined image processing may include any of synchronization processing, gradation correction processing, and color correction processing. The synchronization processing is processing in which image data of each of R, G, and B color components are synchronized with one another. The gradation correction processing is processing in which gradation is corrected for image data. The color correction processing is processing in which color tones are corrected for image data. The image signal processing circuit 31 generates an imaging signal that includes an in-vivo image generated by the image processing described above and that has been processed, which may hereinafter be simply referred to as an imaging signal. The image signal processing circuit 31 may execute gain adjustment according to brightness of the image. The image signal processing circuit 31 is formed using a general-purpose processor, such as a central processing unit (CPU), or a special-purpose processor, such as an arithmetic circuit that executes a specific function, like an application specific integrated circuit (ASIC).

The power supplying circuit 32 supplies electric power generated by the processing device 3, to the endoscope 2.

The transmitting and receiving circuit 33 transmits and receives, for example, a control signal to be transmitted to the endoscope 2 or an image signal output from the endoscope 2, to and from the endoscope 2 via a transmitting and receiving antenna 34.

The transmitting and receiving antenna 34 and the transmitting and receiving antenna 243*c* each form a transmitting and receiving device. Each of these transmitting and receiving antennas 34 and 243*c* may include a circuit or a substrate, which is not illustrated in the drawings.

The processing device 3 includes a control unit that controls driving of components including the imaging element 242 and the light source device 4 and controls input and output of information to and from the components, and the control unit thereby controls the overall system. The control unit is formed using: a general-purpose processor, such as a CPU; or a special-purpose processor, such as an arithmetic circuit that executes a specific function, like an ASIC.

Furthermore, the processing device 3 stores various programs for causing the endoscope system 1 to operate, and data including various parameters needed for the operation of the endoscope system 1. The processing device 3 also includes a storage unit that stores identification information of the processing device 3. The various programs may be widely distributed by being recorded in a computer readable recording medium, such as a hard disk, a flash memory, a CD-ROM, a DVD-ROM, or a flexible disk. These various programs may be acquired by being downloaded via a communication network. The communication network referred to herein is implemented by, for example, any existing public network, a local area network (LAN), or a wide area network (WAN), and may be wired or wireless. The storage unit is implemented using: a read only memory (ROM) including various programs installed therein beforehand, for example; and a RAM or a hard disk storing therein arithmetic parameters and data for processing, for example.

The processing device 3 also includes an input unit that is implemented using any of a keyboard, a mouse, a switch, and a touch panel, and receives input of various signals including an operation instruction signal for instructing operation of the endoscope system 1. The input unit may include a switch provided in the operating unit 22, or a portable terminal, such as an external tablet computer.

The display device 5 displays a display image corresponding to an image signal received from the processing device 3 (the image signal processing circuit 31) via a video cable. The display device 5 is formed using a liquid crystal or organic electroluminescence (EL) monitor, for example.

Figure 3:
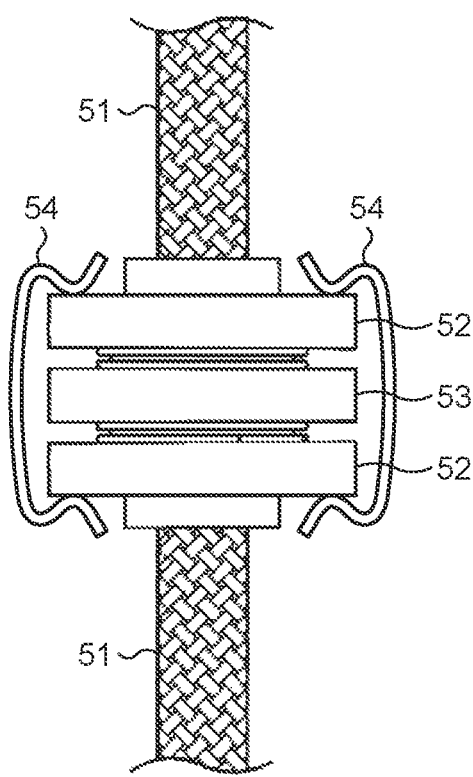
FIG. 3 is a diagram illustrating connection between waveguides.
Figure 4:
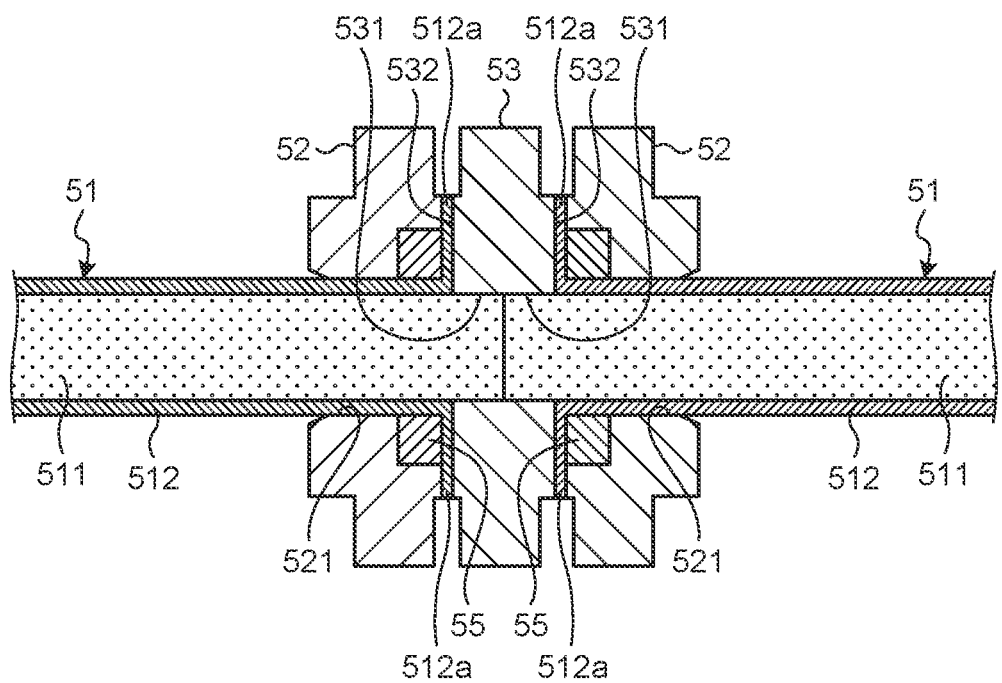
FIG. 4 is a sectional view illustrating the connection between the waveguides.
Figure 5:
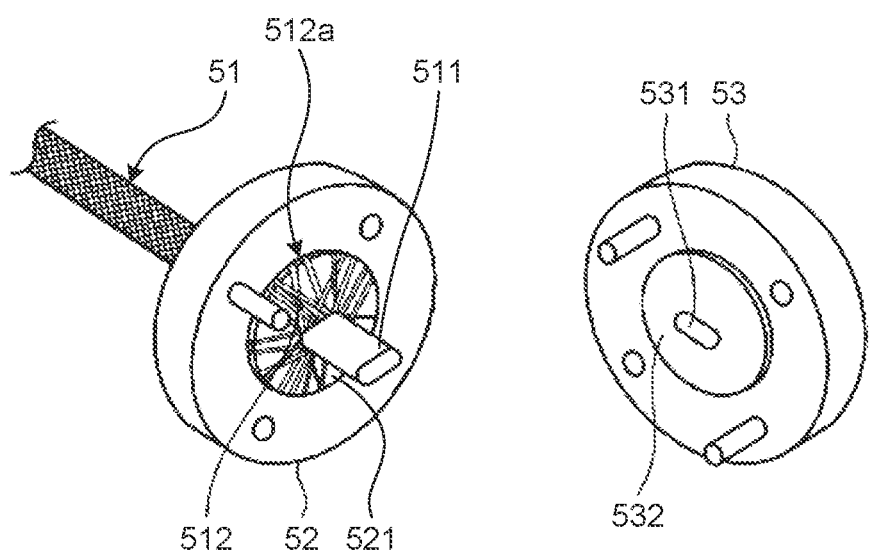
FIG. 5 is a perspective view for explanation of a configuration of a fixing body and a three-dimensional body at a connection between the waveguides.
Figure 6:
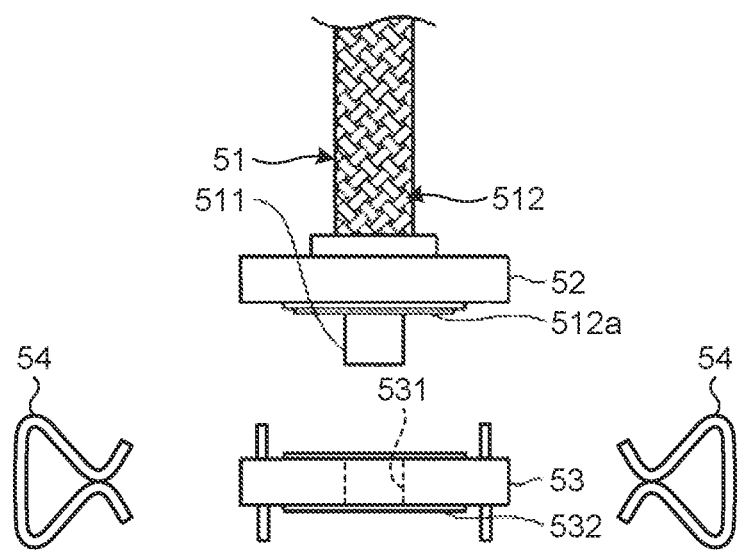
FIG. 6 is an exploded view for explanation of a configuration of the connection between the waveguides.

The transmitting and receiving antenna 243*c* and the transmitting and receiving antenna 34 transmit and receive signals via the waveguide 51. One or plural waveguides are provided in the endoscope 2. A configuration having a plurality of the waveguides 51 connected to each other will be described with respect to this first embodiment. In this first embodiment, the waveguide 51 is connected to the other waveguide/waveguides 51, the connected waveguides 51 extend in the endoscope 2, the transmitting and receiving antenna 243*c* is connected to one end of the waveguides 51, and the transmitting and receiving antenna 34 is connected to the other end of the waveguides 51. A connecting structure for the waveguides 51 will be described by reference to FIG. 3 to FIG. 14. FIG. 3 is a diagram illustrating connection between waveguides. FIG. 4 is a sectional view illustrating the connection between the waveguides. FIG. 5 is a perspective view for explanation of a configuration of a fixing body and a three-dimensional body at a connection between the waveguides. FIG. 6 is an exploded view for explanation of a configuration of the connection between the waveguides. FIG. 4 is a sectional view without pressing aiding members 54 in the connecting structure illustrated in FIG. 3.

The connection between the waveguides will be described first. A fixing body 52 is attached to each of the waveguides 51. The fixing bodies 52 are connected to each other by a three-dimensional body 53. That is, the two waveguides 51 are connected to each other by the three-dimensional body 53 via the fixing bodies 52. Furthermore, the fixing bodies 52 each include an elastic body 55 provided therein.

Figure 7:
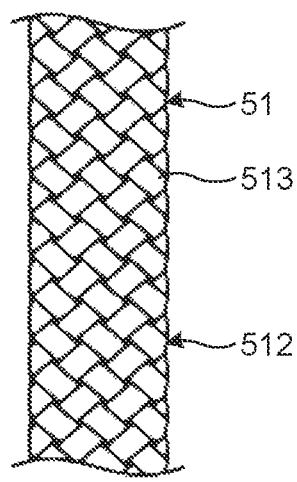
FIG. 7 is a diagram for explanation of a configuration of the waveguides.
Figure 8:
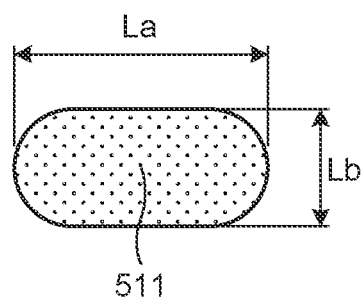
FIG. 8 is a sectional view illustrating a dielectric body forming a part of the waveguide.
Figure 9:
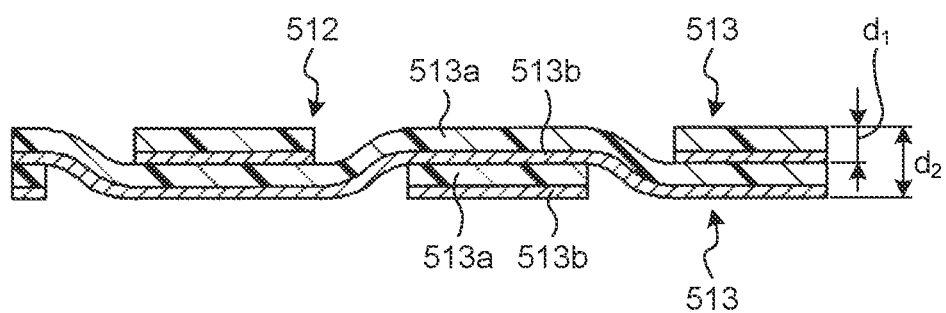
FIG. 9 is a diagram for explanation of the configuration of the waveguides.
Figure 10:
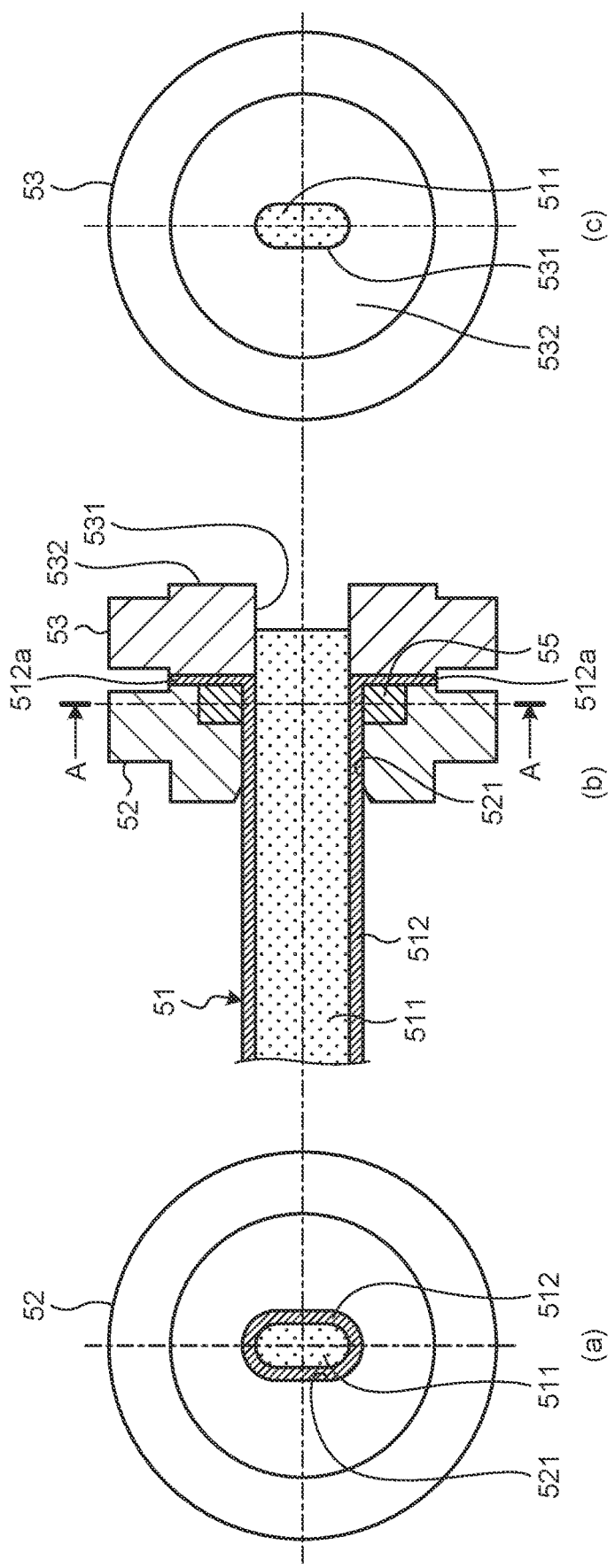
FIGS. 10(a), 10(b), and 10(c) are diagrams for explaining the configuration of the connection between the waveguides.

A configuration of the waveguides 51 will be described by reference to FIG. 7 to FIG. 9. FIG. 7 is a diagram for explanation of a configuration of a waveguide. FIG. 8 is a sectional view illustrating a dielectric body forming a part of the waveguide. FIG. 9 is a sectional view for explanation of the configuration of the waveguide.

The waveguide 51 includes a dielectric body 511 that extends in a bar shape and is flexible, and an external conductor 512 that covers the dielectric body 511 and is electrically conductive.

The dielectric body 511 has a section that is oblate, the section being cut along a plane orthogonal to a longitudinal direction of the dielectric body 511. This section of the dielectric body 511 has a length La in a long axis direction where the section has the longest length, and a length Lb in a short axis direction where the section has the shortest length, this length Lb being less than the length La (see FIG. 8). The longest length in the long axis direction of any oblate shape will hereinafter be referred to as a "long diameter", and the shortest length in the short axis direction of the oblate shape as a "short diameter".

The external conductor 512 is formed of plural flat foil strings 513 that have been braided together, each of the plural flat foil strings 513 being strip-shaped. Specifically, the external conductor 512 is wound around an outer peripheral surface of the dielectric body 511 and the flat foil strings 513 form a braided structure together.

Each of the flat foil strings 513 has a rectangular section cut along a plane perpendicular to a longitudinal direction thereof. Each of the flat foil strings 513 has a structure including a resin film 513a and metallic foil 513b pasted together, the resin film 513a including a non-metallic substance, the metallic foil 513b including a metallic substance. When the flat foil strings 513 have a thickness of $d_1$ and the external conductor 512 has a thickness of $d_2$, the thickness $d_2$ of the external conductor 512 is twice the thickness $d_1$ of the flat foil string 513, for example.

The flat foil strings 513 that have been braided together are arranged, with the metallic foil 513b (lower in FIG. 9) being arranged on the inner side of the external conductor 512 that forms the waveguide 51. That is, the flat foil strings 513 of the external conductor 512 are arranged in position where the metallic foil 513b contacts the outside of the dielectric body 511.

Figure 11:
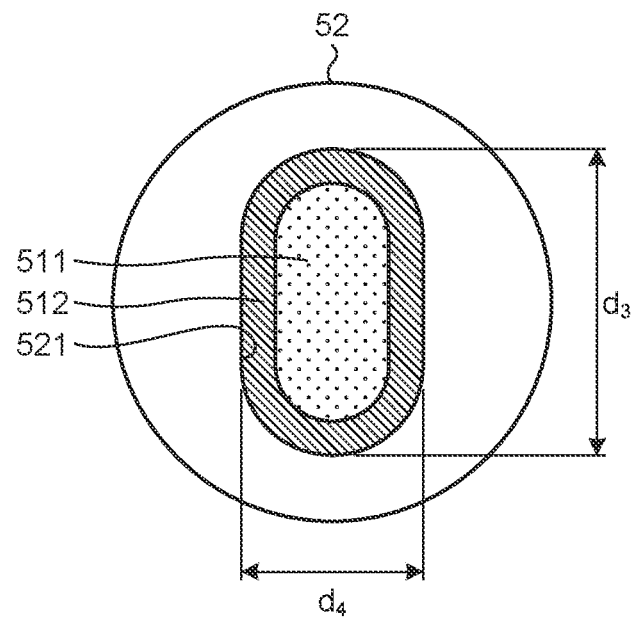
FIG. 11 is an enlarged view of a part of the section illustrated in FIG. 10(a)
Figure 12:
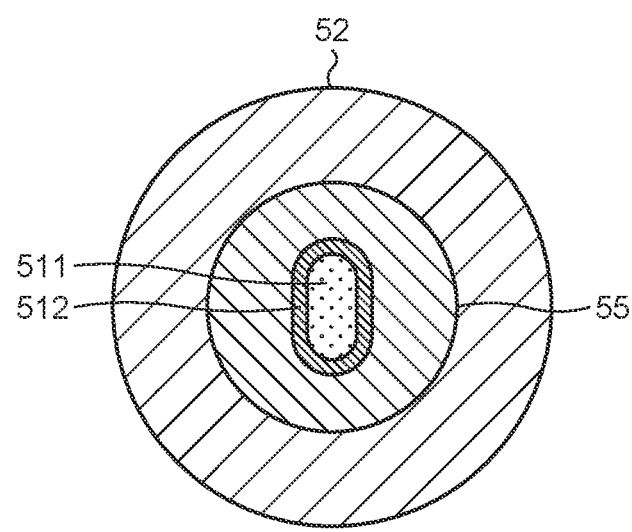
FIG. 12 is a sectional view of the connection between the waveguides, the connection having been cut along a plane corresponding to a line A-A in FIG. 10(b)
Figure 13:
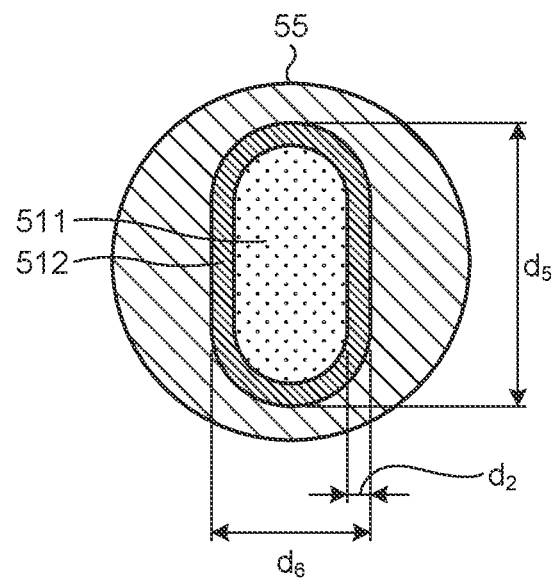
FIG. 13 is an enlarged view of a part of the section illustrated in FIG. 12.
Figure 14:
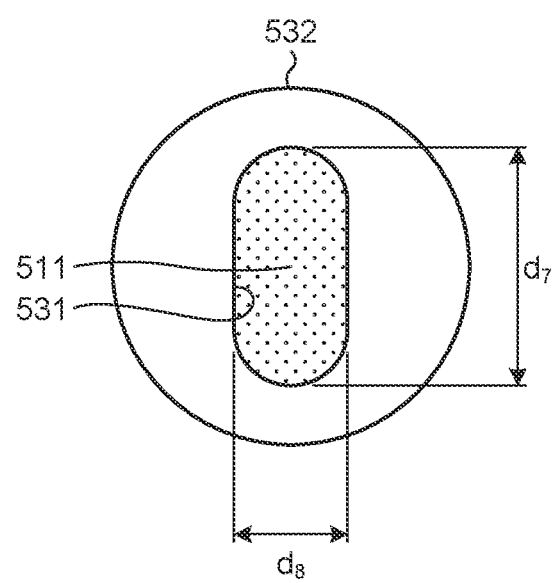
FIG. 14 is an enlarged view of a part of the section illustrated in FIG. 10(c)

FIGS. 10(a), 10(b), and 10(c) are diagrams for explaining a configuration of the connection between the waveguides. FIG. 11 is an enlarged view of a part of the section illustrated in FIG. 10(a). FIG. 12 is a sectional view of the connection between the waveguides, the connection having been cut along a plane corresponding to a line A-A in FIG. 10(b). FIG. 13 is an enlarged view of a part of the section illustrated in FIG. 12. FIG. 14 is an enlarged view of a part of the section illustrated in FIG. 10(c).

FIG. 10(b) is a sectional view illustrating a connection for the waveguide 51, the connection being between the three-dimensional body 53 and one of the fixing bodies 52. FIG. 10(a) is a view of the configuration illustrated in FIG. 10(b), as viewed along a longitudinal direction of the waveguide 51, from the fixing body 52. FIG. 10(c) is a view of the configuration illustrated in FIG. 10(b), as viewed along the longitudinal direction of the waveguide 51, from the three-dimensional body 53. FIGS. 10(a), 10(b), and 10(c) illustrate only the connection between: one of the waveguides 51 and fixing body 52; and the three-dimensional body 53.

The fixing body 52 is a metallic part formed of brass, for example, and holds the elastic body 55. The fixing body 52 includes a through hole 521 formed therein, the through hole 521 being where the waveguide 51 is inserted. The through hole 521 extends in an oblate hole shape. The fixing body 52 is not necessarily a part formed of metal, and may be formed of resin.

An end portion of the waveguide 51 including the external conductor 512 is inserted into the through hole 521 of the fixing body 52. An end portion of the external conductor 512, which is near the three-dimensional body 53, forms a connection enlarging portion 512a by being spread over, still in the form of its braided structure, surfaces of the fixing body 52 and the elastic body 55.

The three-dimensional body 53 is formed using a resin material that is moldable, and includes an electrically conductive surface layer formed on at least faces of the three-dimensional body 53, the faces being faces that come into contact with at least the dielectric body 511 and external conductor 512. The three-dimensional body 53 is, for example, a molded circuit component (a molded interconnect device (MID)) including a metallic film formed on a surface of a resin molded component. The three-dimensional body 53 includes an insertion hole 531 formed therein, the insertion hole 531 being where the dielectric body 511 is inserted. Furthermore, the three-dimensional body 53 includes a protruding portion 532 at an end of the three-dimensional body 53, the end being an end that comes into contact with the fixing body 52. A protruding surface of the protruding portion 532 is a connected surface that comes into contact with the connection enlarging portion 512a. The insertion hole 531 extends in an oblate hole shape. The three-dimensional body 53 have the faces that are electrically conductive, the faces including an inner surface of the insertion hole 531 and being the faces that come into contact with the dielectric body 511 and the external conductor 512. Therefore, the insertion hole 531 has a function equivalent to that of the external conductor 512 of the waveguide 51 and is able to transmit radio waves. The three-dimensional body 53 is not necessarily formed of a resin material, and may be formed of a metallic material, such as brass.

The connection enlarging portion 512a formed of the end portion of the external conductor 512 is fixed by being sandwiched between: the protruding portion 532 of the three-dimensional body 53; and the fixing body 52 and elastic body 55. In this fixed portion, the connection enlarging portion 512a is fixed with the braided structure (the flat foil strings 513) being spread out radially. When fixed, the end portion of the external conductor 512 including the connection enlarging portion 512a is pressed against the three-dimensional body 53 and the dielectric body 511 by a load applied from the elastic body 55. The connection enlarging portion 512a is pressed between the fixing body 52 and the three-dimensional body 53 by a load that the pressing aiding members 54 apply thereto.

Furthermore, by functioning of the external conductor 512 having the braided structure, the waveguide 51 transmits radio waves inside the waveguide 51. That is, the insertion hole 531 of the three-dimensional body 53 and the waveguide 51 both transmit radio waves and electric connection is achieved at the protruding portion 532.

The pressing aiding members 54 hold the fixing body 52 and the three-dimensional body 53 closely to each other along the longitudinal direction of the dielectric body 511. The pressing aiding members 54 are, for example, clips. In this first embodiment, the fixing bodies 52 face each other via the three-dimensional body 53 are held between and pressed by the two pressing aiding members 54. The clips do not necessarily have a special structure, and commercially available clips may be used, for example. FIG. 3 illustrates a configuration using grating clips as an example of the pressing aiding members 54. The pressing aiding members 54 correspond to a holding body.

The elastic body 55 is a ring-shaped member provided on the inner peripheral side of the fixing body 52 and on the outer periphery of the waveguide 51. The waveguide 51 is inserted through a hollow portion in the elastic body 55. The elastic body 55 is formed of a material having resilience to compressive deformation, for example, rubber having elasticity, and is, for example, tubular. The elastic body 55 has an elastic modulus lower than those of the fixing body 52, three-dimensional body 53, and dielectric body 511. The elastic body has, for example, a Shore-A rubber hardness of 20 or more and 70 or less.

An end portion of the dielectric body 511 of the waveguide 51 is inserted into the insertion hole 531 of the three-dimensional body 53. The end portion of the dielectric body 511 is inside the insertion hole 531, and comes into contact with an end portion of the dielectric body 511 of the other waveguide 51 that is inserted from the opposite end of the insertion hole 531, without a clearance between these end portions. Furthermore, the connection enlarging portion 512a is fixed between the fixing body 52 and the protruding portion 532.

A long diameter of the through hole 521 will be denoted by $d_3$, a short diameter of the through hole 521 by $d_4$ (see FIG. 11), a long diameter of an inner circumference of the elastic body 55 by $d_5$, a short diameter of the inner circumference by $d_6$ (see FIG. 13), a long diameter of the insertion hole 531 by $d_7$, and a short diameter of the insertion hole 531 by $d_8$ (see FIG. 14).

The long diameter $d_3$ and short diameter $d_4$ of the through hole 521, and the long diameter $d_5$ and short diameter de of the inner circumference of the elastic body 55 are set correspondingly to an outer circumference of the external conductor 512. For example, the long diameter $d_3$ and the short diameter $d_4$ are slightly larger than lengths resulting respectively from addition of twice the thickness $d_2$ of the external conductor 512 to the long diameter La and short diameter Lb of the section of the dielectric body 511; and the long diameter $d_5$ and short diameter $d_6$ of the inner circumference of the elastic body 55 are approximately equal to lengths resulting respectively from addition of twice the thickness $d_2$ of the external conductor 512 to the long diameter La and short diameter Lb of the section of the dielectric body 511.

The long diameter $d_7$ of the insertion hole 531 is approximately equal to the long diameter La of the dielectric body 511. The short diameter $d_8$ is approximately equal to the short diameter Lb of the dielectric body 511. Conversely, the long diameter La and short diameter Lb of the dielectric body 511 are approximately equal to the long diameter $d_7$ and short diameter de of the insertion hole 531 of the three-dimensional body 53, respectively. Position of the end portion of the waveguide 51 in the insertion hole 531 is thereby determined uniquely.

Being "approximately equal" herein means being identical or including any difference due to manufacturing errors, and refers to, for example, a dimensional setting that allows the dielectric body 511 to be inserted in the insertion hole 531 of the three-dimensional body 53 and that is without looseness.

Figure 15:
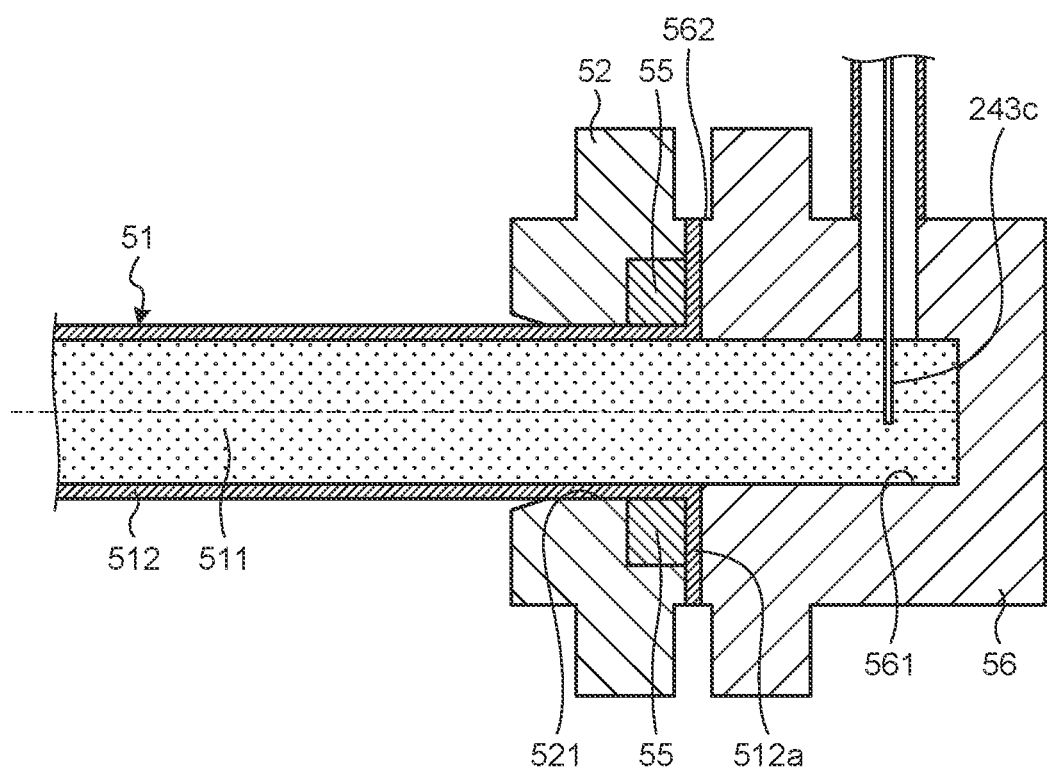
FIG. 15 is a sectional view illustrating a mode of connection between the waveguide and a transmitting and receiving antenna, according to the first embodiment of the disclosure.

Next, a mode of connection between a transmitting and receiving antenna and the waveguide 51 will be described by reference to FIG. 15. FIG. 15 is a sectional view illustrating a mode of connection between a waveguide and a transmitting and receiving antenna according to the first embodiment of the disclosure. Although FIG. 15 illustrates connection between the waveguide 51 and the transmitting and receiving antenna 243c at the distal end portion 24, the same applies to connection between the waveguide 51 and the transmitting and receiving antenna 34. The above described fixing body 52 and a three-dimensional body 56 are attached to an end portion of the waveguide 51. The transmitting and receiving antenna 243c is attached to the three-dimensional body 56, and a hole 561 to house the dielectric body 511 is formed in the three-dimensional body 56. The hole 561 forms space having a shape similar to an outer shape of the dielectric body 511. The hole 561 thus houses the dielectric body 511 without a clearance between the hole 561 and the dielectric body 511. The transmitting and receiving antenna has been inserted into the dielectric body 511 and outputs, as millimeter radio waves, a signal supplied from a coaxial line that is an electric supply line to the antenna, into the waveguide. This structure is called a "coaxial waveguide converter" and is utilized often in this technical field. In this first embodiment, this coaxial waveguide converter functions as a mode converter that converts a mode where propagation though a dielectric body or space is implemented, to a mode where propagation through a conductor is implemented via an antenna.

Furthermore, the three-dimensional body 56 includes a protruding portion 562 at an end of the three-dimensional body 56, the end being an end that comes into contact with the fixing body 52. A protruding surface of the protruding portion 562 is a connected surface that comes into contact with the connection enlarging portion 512a. The connection enlarging portion 512a is fixed between: the protruding portion 562 of the three-dimensional body 56; and the fixing body 52 and elastic body 55. When fixed, the end portion of the external conductor 512 including the connection enlarging portion 512a is pressed against the three-dimensional body 56 and dielectric body 511 by a load exerted from the elastic body 55. The fixing body 52 and the three-dimensional body 56 are pressed by, for example, the pressing aiding members 54.

Figure 16:
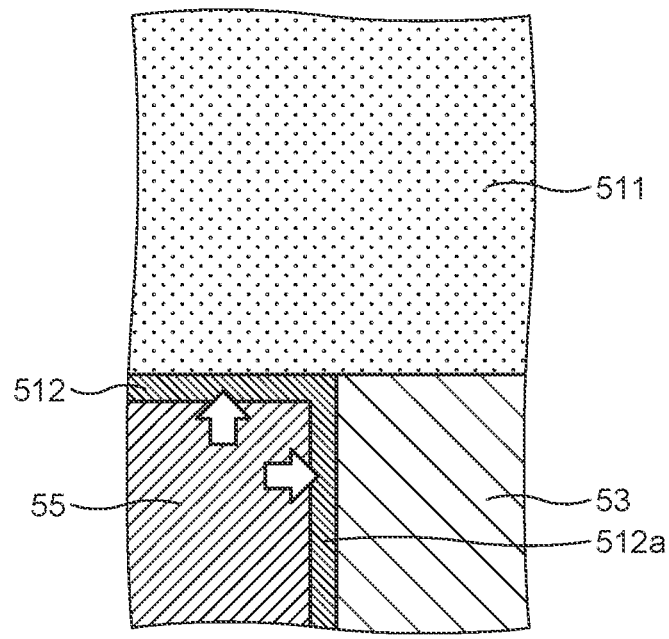
FIG. 16 is a sectional view illustrating a waveguide connecting mode according to the first embodiment of the disclosure.

Next, functions of the connecting structure for the flexible waveguide will be described by reference to FIG. 16. FIG. 16 is a sectional view illustrating a waveguide connecting mode according to the first embodiment of the disclosure. The elastic body 55 causes the external conductor 512 to closely contact the dielectric body 511 and the three-dimensional body 53 by respectively pressing the external conductor 512 interposed between the fixing body 52 and the dielectric body 511 and between the fixing body 52 and the three-dimensional body 53. Although FIG. 16 illustrates the connection between the fixing body 52 and the three-dimensional body 53, the same applies to the connection between the fixing body 52 and the three-dimensional body 56.

Furthermore, as described above, since the elastic body 55 is formed of a material softer than the dielectric body 511; when the waveguides 51, the fixing body 52, the three-dimensional body 53, the pressing aiding members 54, and the elastic body 55 are put together, the external conductor 512 is pressed against the dielectric body 511 by pressing force of the pressing aiding members 54 and dimensions of the elastic body 55 follow the outer shape of the external conductor 512. That is, because the elastic body 55 has elasticity and a hardness smaller than that of the dielectric body 511, even if there is a dimensional difference before assembly, the elastic body 55 is able to be deformed to have the above described dimensions in the assembly.

As a result, connection, at a corner portion of the three-dimensional body 53 (at an opening end), between an inner diameter of the external conductor 512 and the insertion hole 531 of the three-dimensional body 53 becomes smooth and a level difference at that connection is able to be minimized. This minimized level difference is a requirement for reducing loss (reflection) of radio waves at the connecting portion of the waveguide. In particular, the loss (reflection) of radio waves at the connecting portion of the waveguide is able to be reduced by making this level difference 1/50 or less of a wavelength of the radio waves propagated inside the flexible waveguide. The same applies to the connection between the fixing body 52 and the three-dimensional body 56.

When each part (body) is set according to the above described relations between the diameters, the dimension of the inner surface of the external conductor 512 matches the dimension of the outer circumference of the protruding portion 532 that is an end face of the insertion hole 531 that the three-dimensional body 53 has. That is, as described above, "the long diameter La and short diameter Lb of the dielectric body 511 are approximately equal to the long diameter $d_7$ and short dimeter $d_8$ of the insertion hole 531, and position of the end portion of the waveguide 51 is thereby determined uniquely". Furthermore, the form of the external conductor 512 is able to be maintained until the external conductor 512 contacts the protruding portion 532 of the three-dimensional body 53 and the connection is achieved without any level difference at the connection enlarging portion 512a, by making the long diameter $d_5$ and short diameter $d_6$ of the inner circumference of the elastic body 55 approximately equal to dimensions resulting respectively from addition of twice the thickness $d_2$ of the external conductor 512 ($2 \times d_2$) to the long diameter La and short diameter Lb of the dielectric body 511. Connection of the connection enlarging portion 512a at the protruding portion 532 of the three-dimensional body 53 thereby becomes smooth, and as a result, level difference in the connection at the protruding portion 532 of the three-dimensional body 53 is able to be minimized. This minimized level difference is a requirement for reducing loss (reflection) of radio waves at the connecting portion of the waveguide 51. In particular, the loss (reflection) of radio waves at the connecting for the waveguide 51 is able to be reduced by making this level difference 1/50 or less of a wavelength of the radio waves propagated inside the flexible waveguide 51. This level difference corresponds to a clearance between the dielectric body 511 and the external conductor 512 and between the dielectric body 511 and a holding surface of the three-dimensional body 53.

Furthermore, as described above, the connection enlarging portion 512a is fixed by being pressed by the pressing aiding members 54, between the protruding portion 532 of the three-dimensional body 53 and the fixing body 52. When fixed, the connection enlarging portion 512a has its braided structure spread over the connected surface of the protruding portion 532. A side of each of the flat foil strings 513 forming the braided structure faces the connected surface of the protruding portion 532, the side being on the metallic foil 513b. As a result, metal (the metallic foil 513b) of the external conductor 512 of the waveguide 51 and the protruding portion 532 of the three-dimensional body 53 having electric conductivity contact each other, and electric continuity between them is achieved. This electric continuity is a requirement for reducing loss of radio waves (leakage of radio waves) at the connection.

This loss of radio waves tends to be problematic in particular for millimeter radio waves or radio waves in a frequency band higher than that of millimeter radio waves. This is because the shorter the wavelengths of millimeter radio waves or radio waves in a frequency band higher than that of millimeter radio waves are, the more adversely affected the transmission of the radio waves is by slight irregularities on the structure. Specifically, influence of a structure that a medium has on waves not limited to electromagnetic waves is known to be maintained low sufficiently if the size of the structure is kept to about 1/50, the structure not being limited to irregularities and also including non-homogeneity of the medium, for example (see, for example, paragraphs 0094 to 0102 of Japanese Patent Application Laid-open No. 2018-99172). For example, for transmission of 60 GHz millimeter radio waves, the wavelength of the 60 GHz radio waves in free space is 5 mm, and 1/50 of 5 mm is 0.1 mm. Keeping a level difference at an external conductor 0.1 mm or less in a waveguide connecting structure is not easy. However, the connecting structure for the waveguide 51 according to this first embodiment enables the level difference at the external conductor 512 to be kept at 0.1 mm or less easily and smooth connection at the protruding portion 532 to be achieved.

The connection between the fixing body 52 and the three-dimensional body 53 or 56 in the above described first embodiment is configured to cause the external conductor 512 to closely contact the dielectric body 511 and the external conductor 512 (the connection enlarging portion 512a) to closely contact the three-dimensional body 53 or 56, by means of the elastic body 55. According to the first embodiment, the dielectric body 511 closely contacts the dielectric body 511 and the three-dimensional body 53, and loss of radio waves is thus able to be stably reduced when a waveguide including an external conductor having a braided structure is connected to another member.

Furthermore, in the configuration according to the first embodiment, the dimensions of the insertion hole 531 in the three-dimensional body 53 match the cross-sectional shape of the dielectric body 511, the insertion hole 531 having an oblate hole shape, and accurate positioning is thus enabled and assembly of the connecting structure is thus facilitated.

Furthermore, in the first embodiment, just by forming the connection enlarging portion 512a by pressing and spreading the external conductor 512 that has been braided and pressing the connection enlarging portion 512a between the fixing body 52 and the three-dimensional body 53, electric continuity between the external conductor 512 and the three-dimensional body 53 is achieved without adding more components to conventional waveguides.

The connection enlarging portion 512a and the connected surface on the protruding portion 532 of the three-dimensional body 53 may be bonded with an electrically conductive adhesive to achieve electric continuity between the connection enlarging portion 512a and the protruding portion 532 of the three-dimensional body 53. In this case, the connecting structure for the waveguide 51 may be without the fixing body 52 and the pressing aiding members 54. That is, as long as the fixing body 52 and the pressing aiding members 54 are used at the time of bonding, for example, effects equivalent to those in the case where the connecting structure has the fixing body 52 and the pressing aiding members 54 are able to be achieved, the effects including enabling electric connection easily, with the level difference being reduced equivalently to that in the above case.

Furthermore, the through hole 521 in the fixing body 52 according to the first embodiment has the long diameter $d_3$ and the short diameter $d_4$ in all sections of the through hole 521, but as long as the through hole 521 at least has the through hole 521's smallest diameter at the through hole 521's end portion that comes into contact with the three-dimensional body 53 and a long diameter and a short diameter of a section of the through hole 521 in this end portion having the smallest diameter satisfy the above described conditions, that is, $d_3=La+2d_2$ and $d_4=Lb+2d_2$, similar effects are able to be achieved.

It needs to be noted that the waveguide 51 including the external conductor 512 needs to be inserted in the through hole running through the fixing body 52 and the elastic body 55, to obtain the present structure. As described above, the dimensions need to be attained after assembly and fixing, the dimensions being where "the long diameter $d_5$ of the through hole or the hollow portion in the elastic body 55 is approximately equal to a length $(La+2d_2)$ resulting from addition of twice the thickness $d_2$ of the external conductor 512 to the long diameter La of the bar shaped dielectric body 511, and the short diameter $d_6$ thereof is approximately equal to a length $(b+2d_2)$ resulting from addition of twice the thickness $d_2$ of the external conductor 512 to the short diameter Lb of the dielectric body 511", but inserting a waveguide including an external conductor into a through hole of an elastic body is not easy with these dimensions.

However, in the first embodiment, the elastic body 55 undergoes elastic deformation, the diameter of the through hole in the elastic body 55 is thus able to be expanded temporarily, and the ease of assembly is thus able to be improved significantly. For example, if the hole diameter of the through hole in the elastic body 55 is slightly smaller than that according to the above dimensions, assembly will be impossible without elasticity of the elastic body 55, but assembly is possible if the elastic body 55 is elastic.

Furthermore, the dimensions of the through hole 521 in the fixing body 52 according to the first embodiment are slightly larger than the lengths $(La+2d_2)$ and $(Lb+2d_2)$ resulting from addition of twice the thickness $d_2$ of the external conductor 512 to the long diameter La and short diameter Lb of the dielectric body 511, and the problems related to the insertion of the waveguide 51 are thereby mitigated. Even if the dimensions of the through hole 521 in the fixing body 52 are equal to the above described $(La+2d_2)$ and $(Lb+2d_2)$, the assembly is just slightly marred and reduction of reflection at the connection aimed by the disclosure is still able to be achieved.

In this first embodiment, the fixing body 52 that is independent surrounds the elastic body 55 and contributes to connection and fixing of the waveguide 51, but the independent presence of the fixing body 52 or the separate provision of the fixing body 52 and elastic body 55 is not essential. For example, the fixing body 52 and the elastic body 55 according to the first embodiment may be integrated with each other to implement similar functions or such an integrated form may be formed of a material having resilience to compressive deformation to implement similar functions.

First Modified Example of First Embodiment

Figure 17:
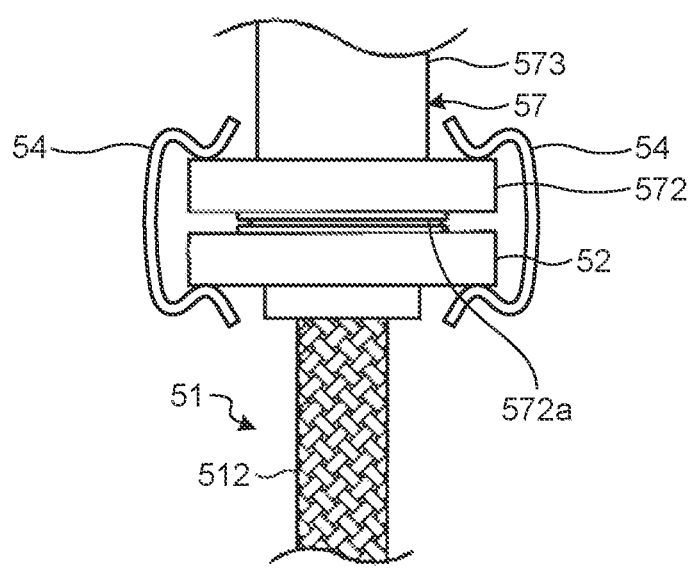
FIG. 17 is a diagram for explanation of a waveguide connecting mode according to a first modified example of the first embodiment of the disclosure.
Figure 18:
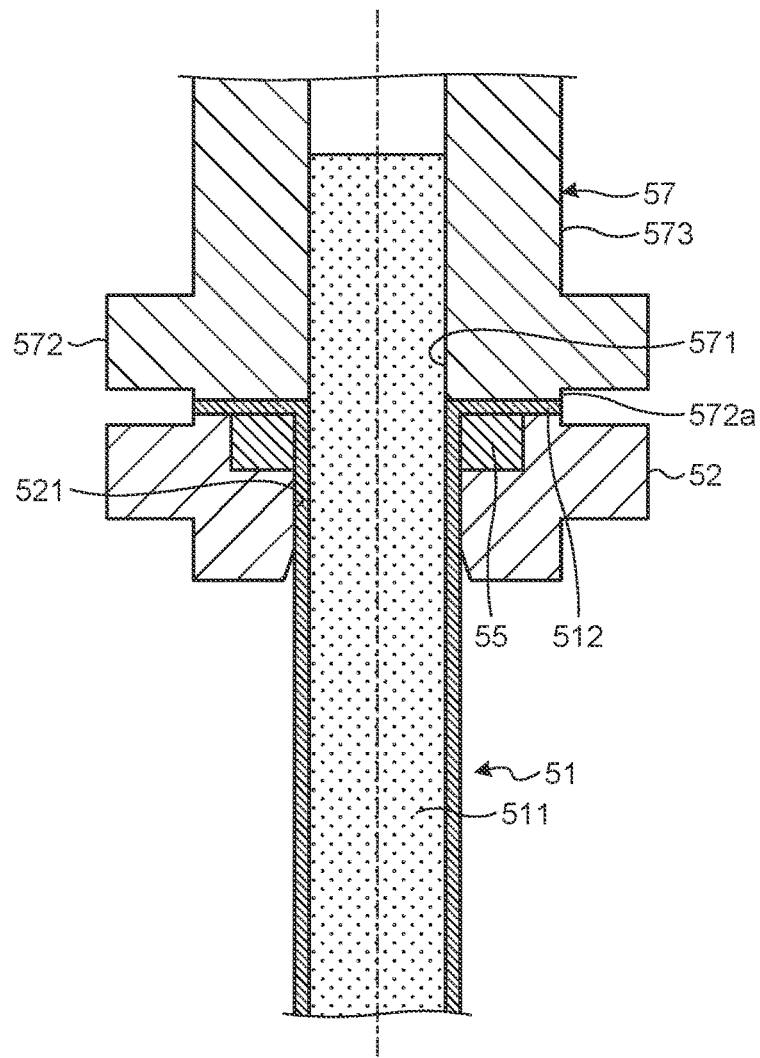
FIG. 18 is a sectional view for explanation of the waveguide connecting mode according to the first modified example of the first embodiment of the disclosure.

Next, a first modified example of the first embodiment of the disclosure will be described by reference to FIG. 17 and FIG. 18. FIG. 17 is a diagram for explanation of a waveguide connecting mode according to the first modified example of the first embodiment of the disclosure. FIG. 18 is a sectional view for explanation of the waveguide connecting mode according to the first modified example of the first embodiment of the disclosure. An endoscope system according to the first modified example has a configuration that is the same as that of the endoscope system 1 described above, except for the waveguide connecting mode. This first modified example includes a three-dimensional body 57 instead of the three-dimensional body 53 according to the first embodiment described above. A configuration (the three-dimensional body 57) different from that according to the first embodiment described above will be described below. A configuration provided in a flexible portion including the two waveguides 51 connected via the three-dimensional body 53 has been described above with respect to the first embodiment, but the three-dimensional body 57 according to the first modified example is provided in, for example, a case where the waveguide 51 is connected to a rigid portion without flexibility.

The three-dimensional body 57 is formed of a resin material that is moldable or a metallic material, such as brass. The three-dimensional body 57 includes an insertion hole 571 formed therein, the insertion hole 571 being where the dielectric body 511 is inserted. Furthermore, the three-dimensional body 57 includes a connecting portion 572 to be connected to the fixing body 52, and an extended portion 573 that extends from the connecting portion 572 in a direction opposite to the fixing body 52. The connecting portion 572 includes a protruding portion 572a at an end of the connecting portion 572, the end being an end that comes into contact with the fixing body 52. A protruding surface of the protruding portion 572a is a connected surface that comes into contact with the connection enlarging portion 512a. Similarly to the insertion hole 531, the insertion hole 571 extends in an oblate hole shape. The three-dimensional body 57 has faces that are electrically conductive, the faces including at least an inner surface of the insertion hole 571 and being faces that come into contact with the dielectric body 511 and the external conductor 512. Therefore, the insertion hole 571 has functions equivalent to those of the external conductor 512 and is able to transmit radio waves.

A transmitting and receiving antenna or an electronic component, for example, is connected to an opposite end of the three-dimensional body 57, the opposite end being opposite to an end of the three-dimensional body 57, the end being near the fixing body 52 (the waveguide 51). Furthermore, the fixing body 52 and the three-dimensional body 57 are pressed by being held between the pressing aiding members 54, for example.

In the first modified example also, the elastic body 55 causes the external conductor 512 to closely contact the dielectric body 511 and the three-dimensional body 57 respectively by pressing the external conductor 512 interposed between the fixing body 52 and the dielectric body 511 and between the fixing body 52 and the three-dimensional body 57.

The above described first modified example has effects similar to the above described effects of the first embodiment.

Second Modified Example of First Embodiment

Figure 19:
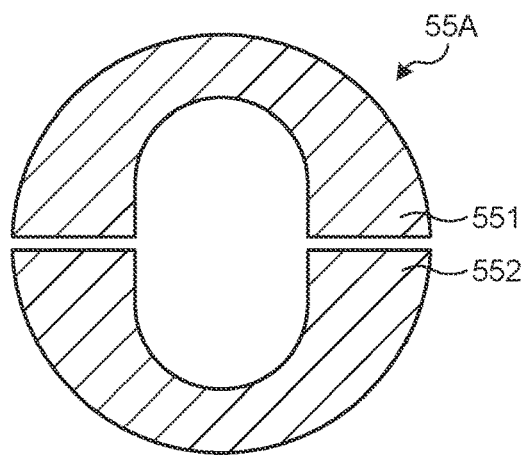
FIG. 19 is a sectional view illustrating a configuration of an elastic body according to a second modified example of the first embodiment of the disclosure.

Next, a second modified example of the first embodiment of the disclosure will be described by reference to FIG. 19. FIG. 19 is a sectional view illustrating a configuration of an elastic body according to the second modified example of the first embodiment of the disclosure. An endoscope system according to the second modified example has a configuration that is the same as that of the endoscope system 1 described above, except for the elastic body. This second modified example includes an elastic body 55A instead of the elastic body 55 according to the first embodiment described above. A configuration (the elastic body 55A) different from that according to the first embodiment described above will be described below.

The elastic body 55A is formed of two component 551 and 552, each having an arch shape. The component 551 and 552 are provided on the outer periphery of the fixing body 52 and surrounds the fixing body 52. The component 551 and 552 are formed by bending sheet-like materials having elasticity.

Similarly to the elastic body 55, the component 551 and 552 of the elastic body 55A cause the external conductor 512 to closely contact the dielectric body 511 and the three-dimensional body 53 by respectively pressing the external conductor 512 that is interposed between the fixing body 52 and the dielectric body 511 and between the fixing body 52 and the three-dimensional body 57. Position of a boundary between the component 551 and 552 is not limited, but if the degree of loss of radio waves is changed by this boundary, the boundary is preferably arranged at a position where the loss is minimized.

The above described second modified example also has effects similar to the above described effects of the first embodiment.

Second Embodiment

Figure 20:
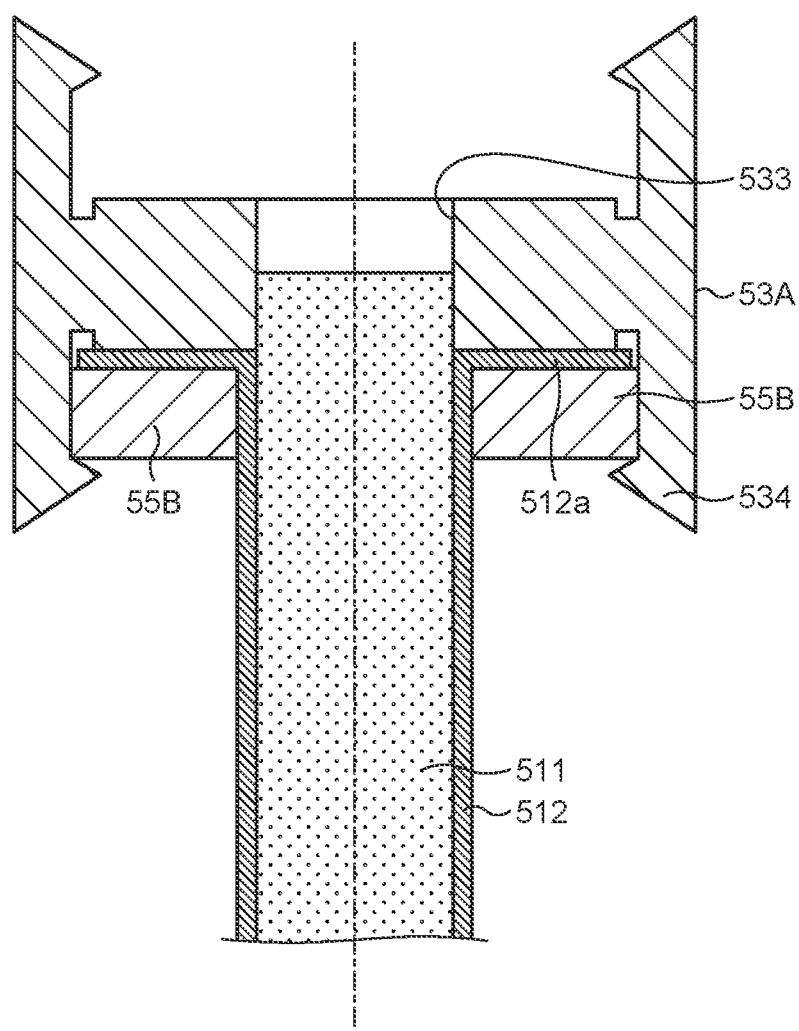
FIG. 20 is a sectional view illustrating a waveguide connecting structure according to a second embodiment of the disclosure.

Next, a second embodiment of the disclosure will be described by reference to FIG. 20. FIG. 20 a sectional view illustrating a connecting structure for a waveguide according to the second embodiment of the disclosure. An endoscope system according to the second embodiment has a configuration that is the same as that of the endoscope system 1 described above, except for the waveguide connecting mode. A configuration different from that of the above described first embodiment will be described below. FIG. 20 illustrates only one of the two waveguides 51 to be connected to each other.

The two waveguides 51 to be connected are connected to each other by a three-dimensional body 53A. Furthermore, the three-dimensional body 53A includes an elastic body 55B provided therein.

The three-dimensional body 53A is formed of a resin material that is moldable or a metallic material, such as brass. The three-dimensional body 53A includes an insertion hole 533 formed therein, the insertion hole 533 being where the dielectric body 511 is inserted. Furthermore, the three-dimensional body 53A includes an engaging portion 534 that engages with the elastic body 55B. The engaging portion 534 houses the elastic body 55B and engages with the elastic body 55B to retain the elastic body 55B. Similarly to the insertion hole 531, the insertion hole 533 extends in an oblate hole shape. The three-dimensional body 53A has faces that are electrically conductive, the faces including at least an inner surface of the insertion hole 533 and being faces that come into contact with the dielectric body 511 and the external conductor 512. Therefore, the insertion hole 533 has functions equivalent to those of the external conductor 512 of the waveguide 51 and is able to transmit radio waves.

The elastic body 55B is a ring-shaped member housed in the engaging portion 534 of the three-dimensional body 53A. By pressing the external conductor 512, the elastic body 55B causes the external conductor 512 to closely contact each of the dielectric body 511 and the three-dimensional body 53A. The elastic body 55B is formed of a material having elasticity.

In the above described configuration of the second embodiment, the three-dimensional body 53A holds the elastic body 55B, and the elastic body 55B causes the external conductor 512 to closely contact the dielectric body 511 and the external conductor 512 to closely contact the three-dimensional body 53A. The second embodiment enables loss of radio waves to be stably reduced in connecting a waveguide to another member, the waveguide including an external conductor having a braided structure.

Modified Example of Second Embodiment

Figure 21:
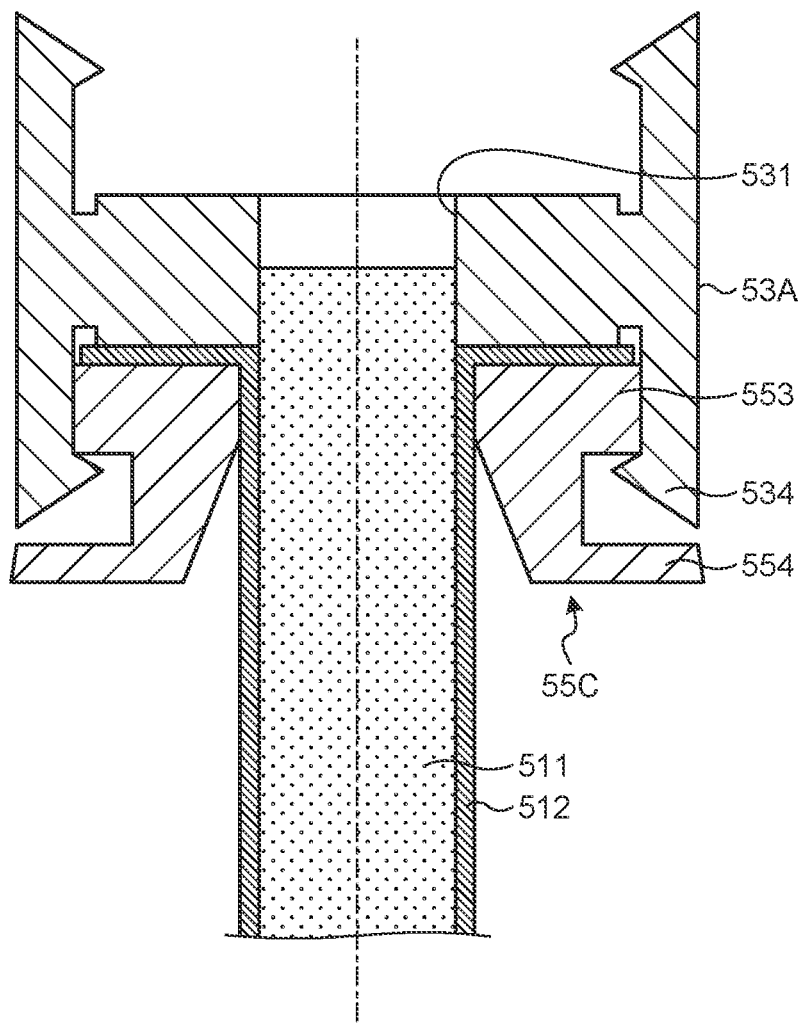
FIG. 21 is a sectional view illustrating a waveguide connecting mode according to a modified example of the second embodiment of the disclosure.

Next, a modified example of the second embodiment of the disclosure will be described by reference to FIG. 21. FIG. 21 is a sectional view illustrating a waveguide connecting mode according to the modified example of the second embodiment of the disclosure. An endoscope system according to this modified example has a configuration that is the same as that of the second embodiment described above, except for the elastic body. This modified example includes an elastic body 55C instead of the elastic body 55B according to the second embodiment described above. A configuration (the elastic body 55C) different from that according to the second embodiment described above will be described below.

The elastic body 55C is ring-shaped, and includes a housed portion 553 that is housed in the engaging portion 534 of the three-dimensional body 53A and a claw portion 554 that protrudes from the housed portion 553. The elastic body 55C causes the external conductor 512 to closely contact each of the dielectric body 511 and the three-dimensional body 53A, by the housed portion 553 pressing the external conductor 512. At least the housed portion 553 of the elastic body 55C is formed of a material having elasticity.

Furthermore, when the claw portion 554 of the elastic body 55C is pushed inward, the housed portion 553 is deformed. By this deformation, the housed portion 553 is able to be easily disengaged from the engaging portion 534.

In this modified example also, the elastic body 55C causes the external conductor 512 to closely contact the dielectric body 511 and the three-dimensional body 53A by respectively pressing the external conductor 512 interposed between the fixing body 52 and the dielectric body 511 and between the fixing body 52 and the three-dimensional body 53A.

The above described modified example also has effects similar to the above described effects of the second embodiment. Furthermore, since the claw portion 554 is provided in the elastic body 55C in this modified example, the elastic body 55C is able to be attached to and removed from the three-dimensional body 53A easily.

Third Embodiment

Figure 22:
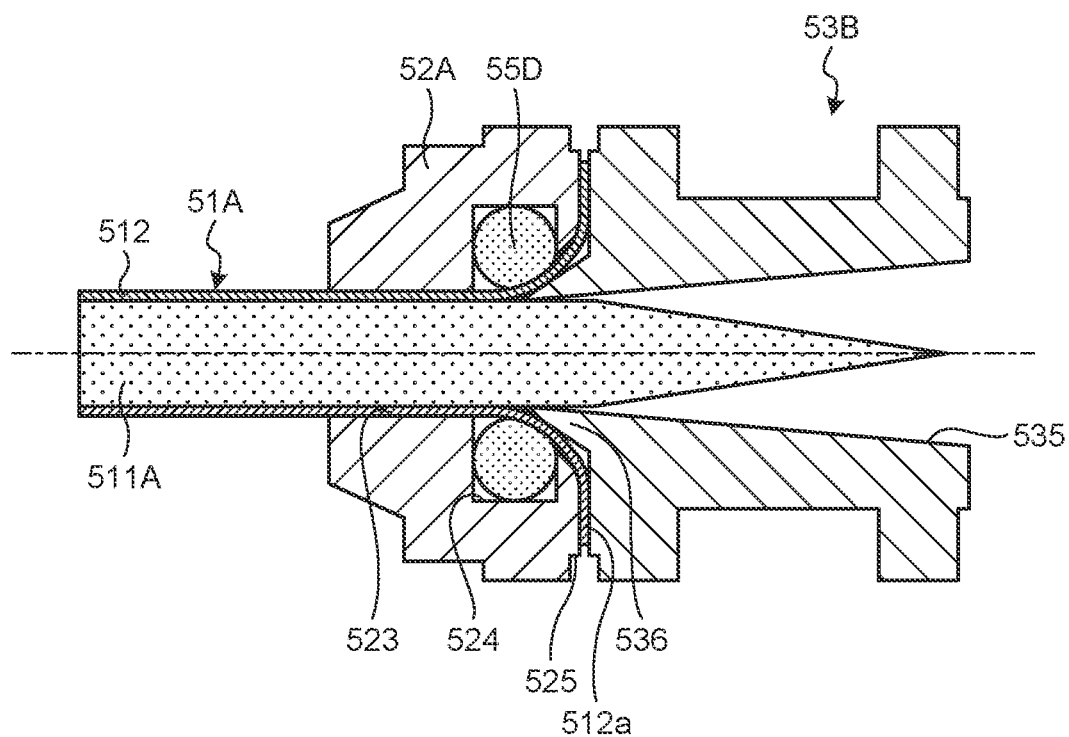
FIG. 22 is a sectional view illustrating a waveguide connecting structure according to a third embodiment of the disclosure.
Figure 23:
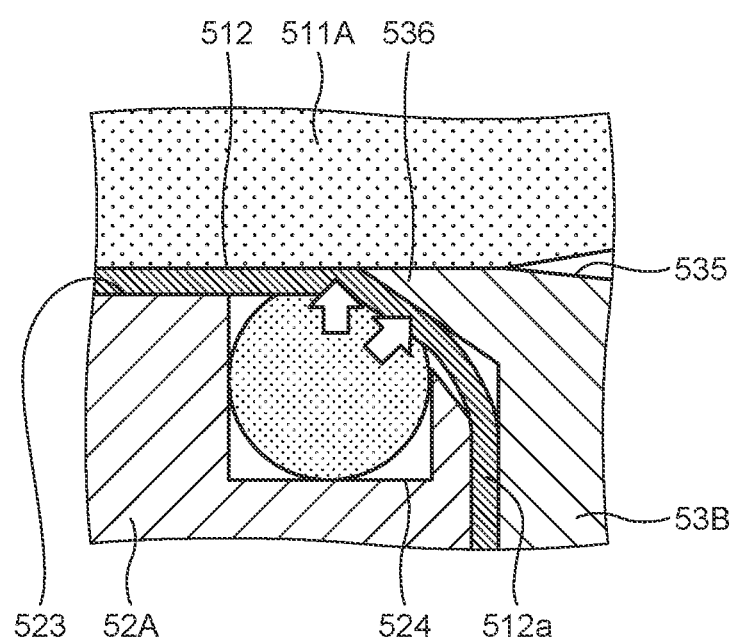
FIG. 23 is an enlarged view of a part of the section illustrated in FIG. 22.

Next, a third embodiment of the disclosure will be described by reference to FIG. 22 and FIG. 23. FIG. 22 a sectional view illustrating a waveguide connecting structure according to the third embodiment of the disclosure. FIG. 23 is an enlarged view of a part of the section illustrated in FIG. 22. An endoscope system according to the third embodiment has a configuration that is the same as that of the endoscope system 1 described above in FIG. 1, except for the waveguide connecting mode. A configuration different from that of the above described first embodiment will be described below. For the third embodiment, a configuration for connecting a waveguide 51A (FIG. 22) to a hollow hole portion is illustrated. A transmitting and receiving antenna or another waveguide, for example, is provided oppositely to the fixing body 52A (near a three-dimensional body 53B) in the hollow hole portion. The waveguide in this third embodiment is a waveguide for a 70 GHz to 80 GHz band, the waveguide including a dielectric body and an external conductor, for example, and the connecting structure according to the third embodiment has a function of connecting this waveguide 51A to a standard transmitting and receiving antenna for a standardized E band (a 60 GHz to 90 GHz band) or to another waveguide.

The waveguide 51A includes a dielectric body 511A extending in a bar shape and having flexibility, and the external conductor 512 covering the dielectric body 511A and being electrically conductive. A fixing body 52A is attached to an end portion of the waveguides 51A. The three-dimensional body 53B is connected to the fixing body 52A.

The dielectric body 511A extends with a section having an oblate shape, the section being cut along a plane orthogonal to a longitudinal direction of the dielectric body 511A, and has a distal end near the three-dimensional body 53B and having a tapered shape. The distal end of the dielectric body 511A is shaped such that a cross-sectional area thereof decreases gradually toward a distal end of the distal end.

The fixing body 52A is a metallic part formed of brass, for example. The fixing bodies 52A includes an elastic body 55D provided therein. Furthermore, a through hole 523 where the waveguide 51A is inserted, and a housing hole 524 that houses the elastic body 55D are formed in the fixing body 52A. The through hole 523 extends in an oblate hole shape. The housing hole 524 is communicated with a part of the through hole 523 and forms a ring-shaped space where the elastic body 55D (FIG. 22) is held. The fixing body 52A may be formed of a single component or may be formed of two or more components.

An end portion of the waveguide 51A including the external conductor 512 is inserted into the through hole 523 of the fixing body 52A. The end portion of the external conductor 512, the end portion being near the three-dimensional body 53B, forms the connection enlarging portion 512a by being radially spread away from the outer periphery of the dielectric body 511A, still in the form of the braided structure, over a surface of the fixing body 52A. Furthermore, a protruding portion 525 (FIG. 22) is provided at an end of the fixing body 52A, the end facing the three-dimensional body 53B. The connection enlarging portion 512a radially spread away from the outer periphery of the dielectric body 511A, over a protruding surface of the protruding portion 525.

The three-dimensional body 53B is formed of a resin material that is moldable or a metallic material, such as brass. The three-dimensional body 53B includes an insertion hole 535 formed therein, the insertion hole 535 being where the dielectric body 511A is inserted. The insertion hole 535 forms a tapered space extending in an oblate hole shape and providing an opening that becomes larger with increasing distance from the fixing body 52A. That is, in the connecting structure illustrated in FIG. 22, the smaller the size of the dielectric body 511A becomes, the larger the size of the opening of the insertion hole 535 becomes.

Furthermore, a sharp portion 536 that protrudes toward the fixing body 52A is provided at a portion of the three-dimensional body 53B, the portion being interposed between the elastic body 55D and the dielectric body 511A. The sharp portion 536 is provided around the opening of the insertion hole 535 and protrudes in a direction parallel to a penetrating direction of the insertion hole 535. The sharp portion 536 has a section with a distal end forming an acute angle, the section being cut along a plane parallel to the penetrating direction of the insertion hole 535. This angle of the distal end of the sharp portion 536 is set at, for example, 45° or more and 60° or less. The sharp portion 536 is positioned in a space formed between a radially spreading portion of the external conductor 512 (the connection enlarging portion 512a) and the dielectric body 511A. Protruding faces of the sharp portion 536 serve as a connected surface that comes into contact with each of the connection enlarging portion 512a and the dielectric body 511A.

The three-dimensional body 53B has faces that are electrically conductive, the faces including at least an inner surface of the insertion hole 535 and being faces that come into contact with the dielectric body 511A and the external conductor 512. Therefore, the insertion hole 535 has functions equivalent to those of the external conductor 512 in the waveguide 51A and functions as a hollow waveguide that transmits radio waves.

Connection between the fixing body 52A and the three-dimensional body 53B is aided by the pressing aiding members 54 described above with respect to FIG. 3, for example.

The elastic body 55D is a ring-shaped member housed in the housing hole 524 of the fixing body 52A. The elastic body 55D has a circular section (see FIG. 22), for example. By pressing the external conductor 512, the elastic body 55D causes the external conductor 512 to closely contact each of the dielectric body 511A and the three-dimensional body 53B (the sharp portion 536). The elastic body 55D is formed of a material having elasticity.

The elastic body 55D is a rubber ring having a Shore-A rubber hardness of 20 or more and 70 or less, for example, a Shore-A rubber hardness of about 30. The elastic body 55D has an inner diameter slightly smaller than an outer circumference of the waveguide 51A. When installing the elastic body 55D on the waveguide 51A, the waveguide 51A is inserted in the elastic body 55D that has been expanded. In this state, the elastic body 55D slightly tightens the waveguide 51A. However, because the elastic body 55D is formed of a material softer than the dielectric body 511A, when the components are installed, the elastic body 55D presses the external conductor 512 against the dielectric body 511A and dimensions of the elastic body 55D naturally follow the outer shape of the external conductor 512. Furthermore, when the connection enlarging portion 512a is formed in the external conductor 512 while the waveguide 51A is inserted into the through hole 523; the tightening force of the elastic body 55D prevents the external conductor 512 from extending more than necessary, and serves to smoothly expand the shape of the braided external conductor 512 around the sharp portion 536 to follow a shape from the dielectric body 511A to the sharp portion 536 and the connected surface.

The third embodiment described above is configured such that the elastic body 55D causes the external conductor 512 to closely contact the dielectric body 511A and the external conductor 512 to closely contact the sharp portion 536 of the three-dimensional body 53B. This third embodiment enables loss of radio waves to be stably reduced in connecting a waveguide to another member, the waveguide including an external conductor having a braided structure.

Furthermore, according to the third embodiment, when the three-dimensional body 53B is connected to the fixing body 52A including the waveguide 51A arranged therein, the sharp portion 536 comes between the dielectric body 511A and the external conductor 512 and presses the external conductor 512 to radially spread away from the outer periphery of the dielectric body 511A, and the sharp portion 536 thus contributes to the formation of the connection enlarging portion 512a. As a result, the connection enlarging portion 512a is able to be formed efficiently in the waveguide 51A.

Fourth Embodiment

Figure 24:
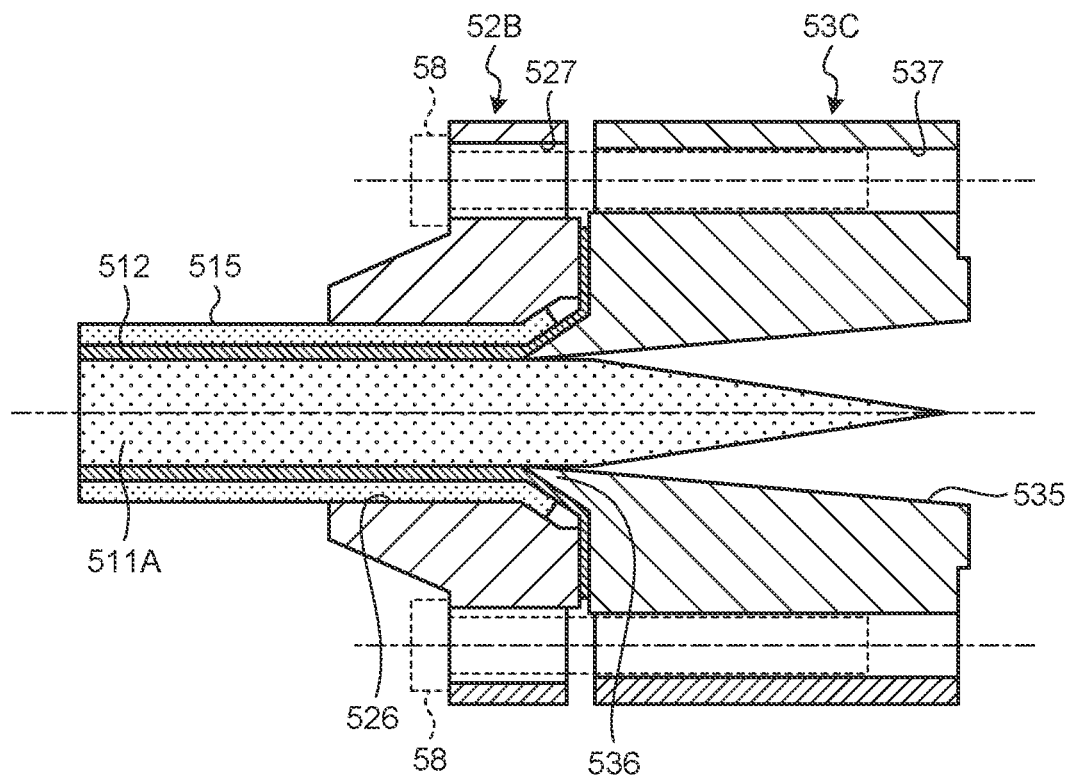
FIG. 24 is a sectional view illustrating a waveguide connecting structure according to a fourth embodiment of the disclosure.
Figure 25:
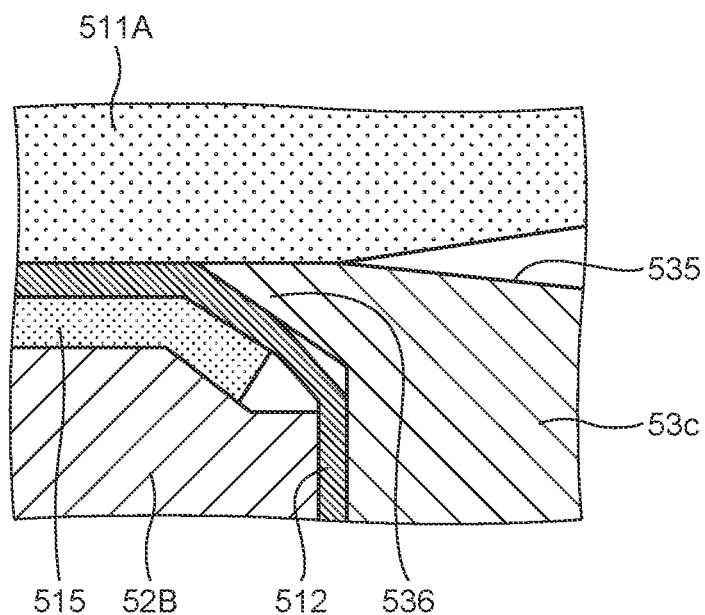
FIG. 25 is an enlarged view of a part of the section illustrated in FIG. 24.
Figure 26:
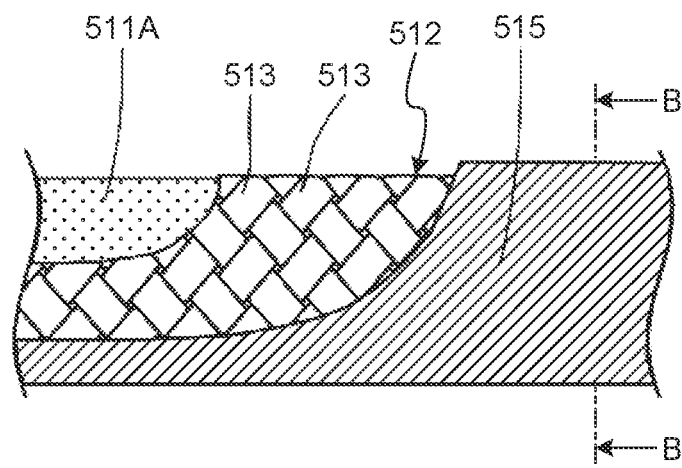
FIG. 26 is a diagram for explanation of a configuration of a waveguide according to the fourth embodiment of the disclosure.
Figure 27:
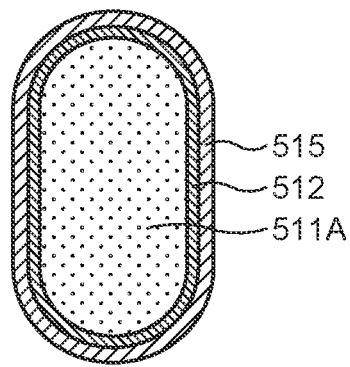
FIG. 27 is a sectional view taken upon a line B-B illustrated in FIG. 26.

Next, a fourth embodiment of the disclosure will be described by reference to FIG. 24 and FIG. 25. FIG. 24 a sectional view illustrating a waveguide connecting structure according to the fourth embodiment of the disclosure. FIG. 25 is an enlarged view of a part of the section illustrated in FIG. 24. FIG. 26 is a diagram for explanation of a configuration of a waveguide according to the fourth embodiment of the disclosure. FIG. 27 is a sectional view taken upon a line B-B illustrated in FIG. 26. An endoscope system according to the fourth embodiment has a configuration that is the same as that of the endoscope system 1 described above, except for the waveguide connecting mode. A configuration different from that of the above described first embodiment will be described below. For the fourth embodiment, a configuration for connecting the waveguide 51A to a hollow hole portion is illustrated. A transmitting and receiving antenna or another waveguide, for example, is provided oppositely to a fixing body 52B (near a three-dimensional body 53C) in the hollow hole portion.

The fixing body 52B is a metallic part formed of brass, for example. The fixing body 52B includes a through hole 526 formed therein, the through hole 526 being where the waveguide 51A is inserted. The through hole 526 extends in an oblate hole shape.

The three-dimensional body 53C is formed of a resin material that is moldable or a metallic material, such as brass. The three-dimensional body 53C includes an insertion hole 535 formed therein, the insertion hole 535 being where the dielectric body 511A is inserted. Furthermore, a sharp portion 536 is provided at an end of the three-dimensional body 53C, the end being an end that comes into contact with the fixing body 52B. The three-dimensional body 53C has faces that are electrically conductive, the faces including at least an inner surface of the insertion hole 535 and being faces that come into contact with the dielectric body 511A and the external conductor 512.

The fixing body 52B and the three-dimensional body 53C are fastened to each other with a screw 58, for example. Specifically, the screw 58 is inserted into a through hole 527 formed in the fixing body 52B and screwed into a screw hole 537 formed in the three-dimensional body 53C.

In this fourth embodiment, a protective tube 515 covering the outer periphery of the external conductor 512 is provided in the waveguide 51A (see FIG. 26 and FIG. 27). The protective tube 515 is a tubular member made of rubber having carbon kneaded therein, the tubular member having elasticity. The protective tube 515 has, in addition to a role of protecting the waveguide 51A, a role of preventing leakage of millimeter waves from the waveguide 51A by the presence of carbon kneaded therein. In addition, the protective tube 515 extends to the vicinity of an end portion of the fixing body 52B, the end portion being near the three-dimensional body 53C, and functions as an elastic body that presses the external conductor 512 against the dielectric body 511A and three-dimensional body 53C. The protective tube 515 has a Shore-A rubber hardness of 20 or more and 70 or less, a Shore-A rubber hardness of 50.

The protective tube 515 is inserted into the through hole 526 of the fixing body 52B. Furthermore, an end portion of the protective tube 515 is positioned at an end portion of the fixing body 52B, the fixing body 52B's end portion being near the three-dimensional body 53C, and the dielectric body 511A and the external conductor 512 extend out from the end portion of the fixing body 52B. In addition, the end portion of the external conductor 512, the end portion being near the three-dimensional body 53B, forms the connection enlarging portion 512a by being spread over, still in the form of its braided structure, a surface of the fixing body 52B.

In the fixing body 52B, the protective tube 515 causes the external conductor 512 to closely contact each of the dielectric body 511A and the three-dimensional body 53C (the sharp portion 536) by pressing the external conductor 512.

The fourth embodiment described above is configured such that the protective tube 515 causes the external conductor 512 to closely contact the dielectric body 511A and the external conductor 512 to closely contact the sharp portion 536 of the three-dimensional body 53C. This fourth embodiment enables loss of radio waves to be stably reduced in connecting a waveguide to another member, the waveguide including an external conductor having a braided structure.

Furthermore, the provision of the protective tube 515 functioning as an elastic body on the waveguide 51A according to the fourth embodiment facilitates assembly of the connecting structure while enabling the external conductor 512 to closely contact the dielectric body 511A and three-dimensional body 53C.

Fifth Embodiment

Figure 28:
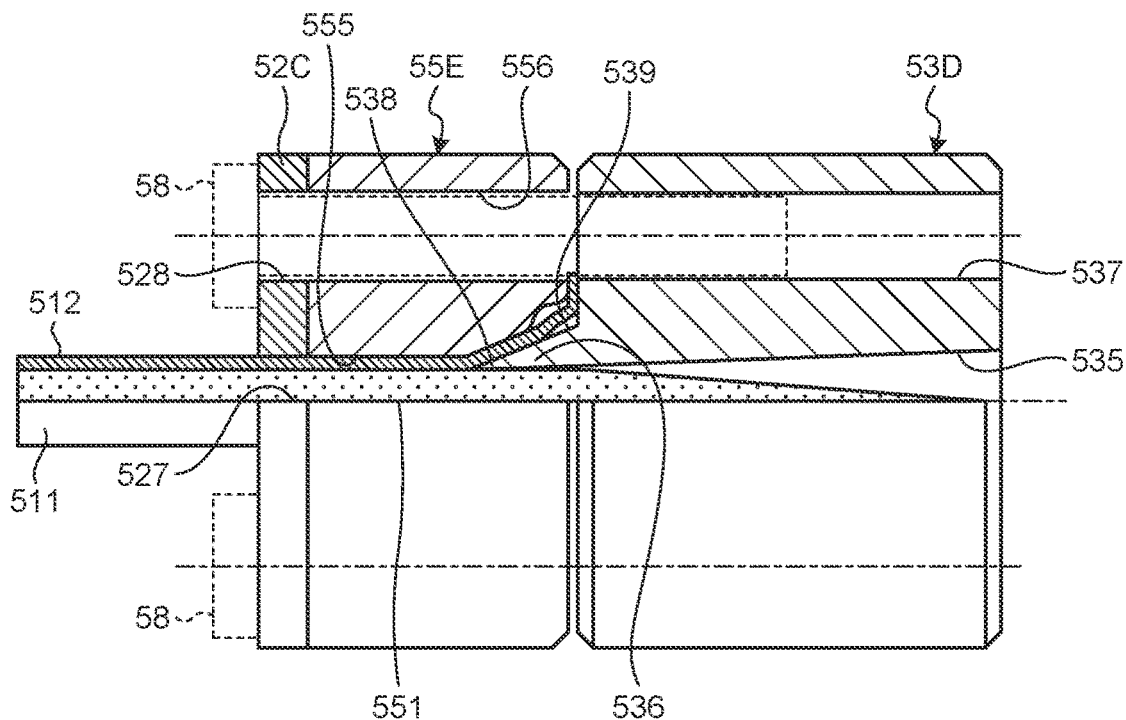
FIG. 28 is a sectional view illustrating a waveguide connecting structure according to a fifth embodiment of the disclosure.
Figure 29:
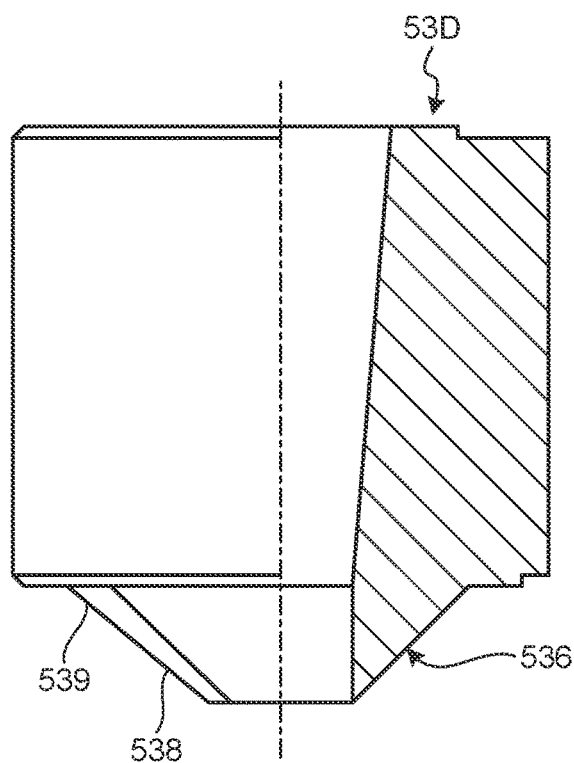
FIG. 29 is a partial sectional view illustrating a three-dimensional body according to the fifth embodiment of the disclosure.
Figure 30:
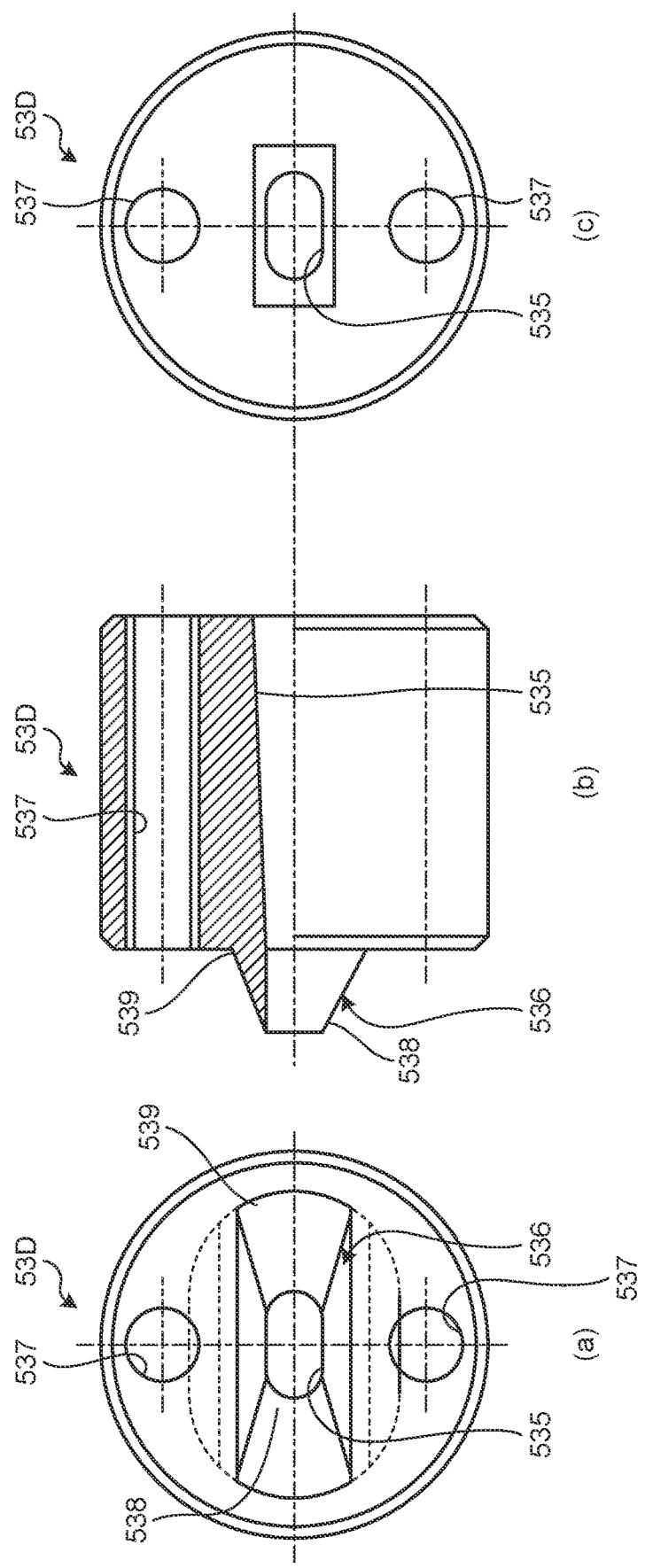
FIGS. 30(a), 30(b), and 30(c) are plan views for explaining a configuration of a fixing body and the three-dimensional body at a connection of a waveguide.

Next, a fifth embodiment of the disclosure will be described by reference to FIG. 28 to FIG. 32. FIG. 28 is a partial sectional view illustrating a waveguide connecting structure according to the fifth embodiment of the disclosure. FIG. 29 is a partial sectional view illustrating a three-dimensional body according to the fifth embodiment of the disclosure. FIGS. 30(a), 30(b), and 30(c) are plan views for explaining a configuration of a fixing body and the three-dimensional body at a junction of the waveguide. An endoscope system according to the fifth embodiment has a configuration that is the same as that of the endoscope system 1 described above, except for the waveguide connecting mode. A configuration different from that of the above described first embodiment will be described below. For the fifth embodiment, a configuration for connecting the waveguide 51A to a hollow hole portion is illustrated. A transmitting and receiving antenna or another waveguide, for example, is provided oppositely to a fixing body 52C (near a three-dimensional body 53D) in the hollow hole portion.

The fixing body 52C is a metallic part formed of brass, for example. The fixing body 52C has a circular disk shape that is hollow. The fixing body 52C includes a through hole 528 formed therein, the through hole 528 being where the waveguide 51A is inserted. The through hole 528 extends in an oblate hole shape.

The three-dimensional body 53D is formed of a resin material that is moldable or a metallic material, such as brass. The three-dimensional body 53D includes an insertion hole 535 formed therein, the insertion hole 535 being where the dielectric body 511A is inserted. Furthermore, a sharp portion 536 is provided at an end of the three-dimensional body 53D, the end being an end that comes into contact with the fixing body 52C. The three-dimensional body 53D has faces that are electrically conductive, the faces including at least an inner surface of the insertion hole 535 and being faces that come into contact with the dielectric body 511A and the external conductor 512.

The fixing body 52C and the three-dimensional body 53D are fastened to each other with the screw 58, for example.

The sharp portion 536 includes an extended portion 538 that extends to form an acute angle, and a base portion 539 that supports the extended portion 538. Thickness of the base portion 539 at the long side of its opening having an oblate shape is thinner than thickness of the base portion 539 at the short side of the opening. This means that thickness of the sharp portion 536 at a portion of a cross-sectional shape of the dielectric body 511A, the portion having a larger curvature radius, is thinner than thickness of the sharp portion 536 at a portion of the cross-sectional shape of the dielectric body 511A, the portion having a smaller curvature radius, these portions facing the sharp portion 536. The sharp portion 536 is able to be shaped like this because the three-dimensional body 53D according to the fifth embodiment is manufactured by transfer molding in which resin, at the time of molding, is brought into a state where the resin is low in viscosity and nearly liquid and the resin thus reaches corners of the molds. Because sharpness of a distal end of the extended portion 538 is an important requirement for implementing smooth connection without any depression at a connection, that is, for reducing loss (reflection) at the connection, in this fifth embodiment, transfer molding can be said to be an optimal means for manufacturing the three-dimensional body 53D by resin molding.

An elastic body 55E is a member that is ring-shaped and held between the fixing body 52C and the three-dimensional body 53D. By pressing the external conductor 512, the elastic body 55E causes the external conductor 512 to closely contact each of the dielectric body 511A and the three-dimensional body 53D (the sharp portion 536). The elastic body 55E is formed of a material having elasticity. The elastic body 55E is formed of, for example, a rubber material having a rubber hardness of about A65 degrees. The elastic body 55E according to the fifth embodiment includes a through hole 555 formed therein, the through hole 555 being where the waveguide 51A is inserted. The through hole 555 has an oblate cross-sectional shape having a long diameter and a short diameter that are approximately equal to the outer shape (a long diameter and a short diameter of an oblate cross-sectional shape) of the waveguide 51A including the external conductor 512, and an opening of the through hole 555 has a shape that smoothly increases in diameter to follow the shape of the three-dimensional body 53D from the sharp portion 536 to a connected surface of the three-dimensional body 53D, the opening being at an end of the through hole 555, the end facing the three-dimensional body 53D at the time of assembly. By pressing the connection enlarging portion 512a of the external conductor 512 along the three-dimensional body 53D from the sharp portion 536 to the connected surface of the three-dimensional body 53D, the elastic body 55E is able to press and fix the external conductor 512 and its connection enlarging portion 512a against the dielectric body 511A, the sharp portion 536, and the connected surface while keeping the smooth shape of the external conductor 512 and connection enlarging portion 512a.

The elastic body 55E, the three-dimensional body 53D, and the waveguide 51A are fixed by using the washer-like fixing body 52C that has been manufactured by laser-cutting a metallic plate and fastening with the screw 58. A screw through hole 556 where the screw 58 penetrates through is formed in the elastic body 55E and a screw hole (a female hole) 537 including a screw thread threaded therein is formed in the three-dimensional body 53D, the screw thread being necessary for fastening.

Figure 31:
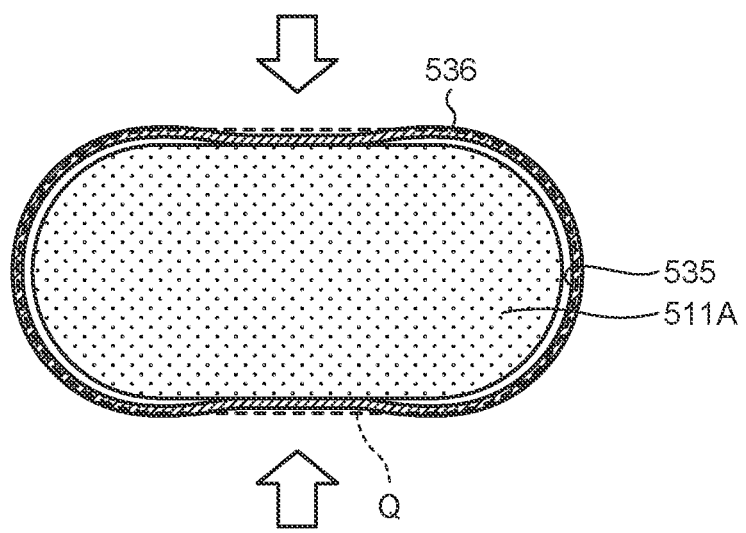
FIG. 31 is a first diagram illustrating a state of the waveguide when an elastic body is pressed against the waveguide.
Figure 32:
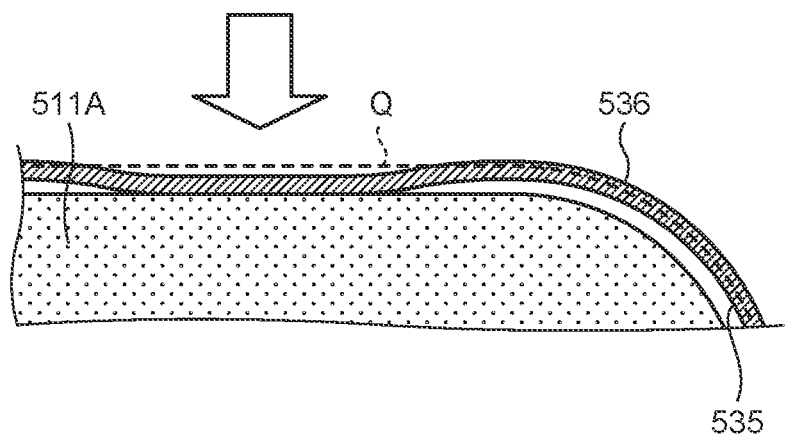
FIG. 32 is a second diagram illustrating the state of the waveguide when the elastic body is pressed against the waveguide.

FIG. 31 and FIG. 32 are diagrams illustrating a state of a waveguide when an elastic body is pressed against the waveguide. A broken line Q represents the shape of the sharp portion 536 before deformation. The elastic body 55E is pressed against the three-dimensional body 53D with pressing force by the screw 58 via the fixing body 52C. To prevent the elastic body 55E from moving outward when being pressed, bumps and dips for preventing such movement and not illustrated in the drawings are formed on contacting surfaces of the three-dimensional body 53D and elastic body 55E. By these bumps and dips of the three-dimensional body 53D and elastic body 55E fitting each other, the pressing force by the screw 58 is properly converted to the force of pressing the external conductor 512 and connection enlarging portion 512a against and along the three-dimensional body 53D from the sharp portion 536 to the connected surface of the three-dimensional body 53D.

The three-dimensional body 53D is formed of a resin material softer (=having a smaller Young's modulus) than metal, a long side portion at the opening of the three-dimensional body 53D is formed more thinly than a short side portion at the opening of the three-dimensional body 53D, the opening being where the waveguide 51A is connected to, the long side portion is slightly deformed by the pressing force, and the extended portion 538 along the long diameter closely contact the waveguide 51A's core member.

Although the first embodiment described above is based on the premise that the long diameter La and short diameter Lb of the dielectric body 511 are approximately equal to the long diameter and short diameter of the opening to which the waveguide 51 is connected to, that is, the oblate opening; the three-dimensional body 53D according to the fifth embodiment is able to be deformed slightly and thus even if the dimensions of the dielectric body 511 are slightly thinner, the long diameter portion at the opening having the sharp portion 536 is able to be pressed against and caused to follow the dielectric body 511. As a result, level difference at the long diameter portion is able to be minimized. Minimizing the level difference at the long diameter portion serves to minimize loss (reflection) at the connection, the minimization of loss being aimed by the disclosure. This is because a difference between short diameters governs reflection at a connection in a waveguide (see Fujio Ishihara, "Equivalent Characteristic Impedance Formula of Waveguide and Its Applications", Transactions of the Institute of Electronics, Information and Communication Engineers, January 1992). That is, due to the form in which the extended portion 538 of the sharp portion 536 and the base portion 539 supporting the extended portion 538 are smaller in thickness along the long diameter of their oblate cross sectional shapes than along the short diameter of their oblate cross sectional shapes; the level difference at their long diameter portions is minimized (dimensions of the short diameters are able to be made to match each other at the central portion of the waveguide 51A) and reflection at the connection is thus able to be reduced even more effectively.

The slight deformation in the diameter of the opening at the connection is very useful in determining the mode of connection for the waveguide 51A having a small diameter, the waveguide 51A being used for millimeter waves, in particular, for frequencies of the E-band or higher. This is because the cross-sectional shape of the dielectric body 511A, among the components forming the connecting structure of the disclosure, is difficult to be made constant, and the structure enables the variation in the cross-sectional shape described above to be absorbed. In terms of cost, the dielectric body 511A is desirably manufactures by extrusion molding, but due to characteristics of extrusion molding, variation in the shape of the dielectric body 511A is more likely to occur than that in those of other components. The smaller the diameter of a waveguide is, the larger the influence of this variation on properties of the connection, and specifically, waveguides having a short diameter of about 1 mm or less are significantly affected. These waveguides having a short diameter of about 1 mm correspond to waveguides for E-band (60 GHz to 90 GHZ) according to the waveguide standards.

The fifth embodiment described above is configured such that the elastic body 55E causes the external conductor 512 to closely contact the dielectric body 511A and the external conductor 512 to closely contact the sharp portion 536 of the three-dimensional body 53D. The fifth embodiment enables loss of radio waves to be stably reduced in connecting a waveguide to another member, the waveguide including an external conductor having a braided structure.

Furthermore, according to the fifth embodiment, when the fixing body 52C, the elastic body 55E, and the three-dimensional body 53B are connected, the sharp portion 536 comes between the dielectric body 511A and the external conductor 512 and presses the external conductor 512 to spread the external conductor 512, and the sharp portion 536 thus contributes to the formation of the connection enlarging portion 512a. As a result, the connection enlarging portion 512a is able to be formed efficiently in the waveguide 51A.

Modified Example of Fifth Embodiment

Figure 33:
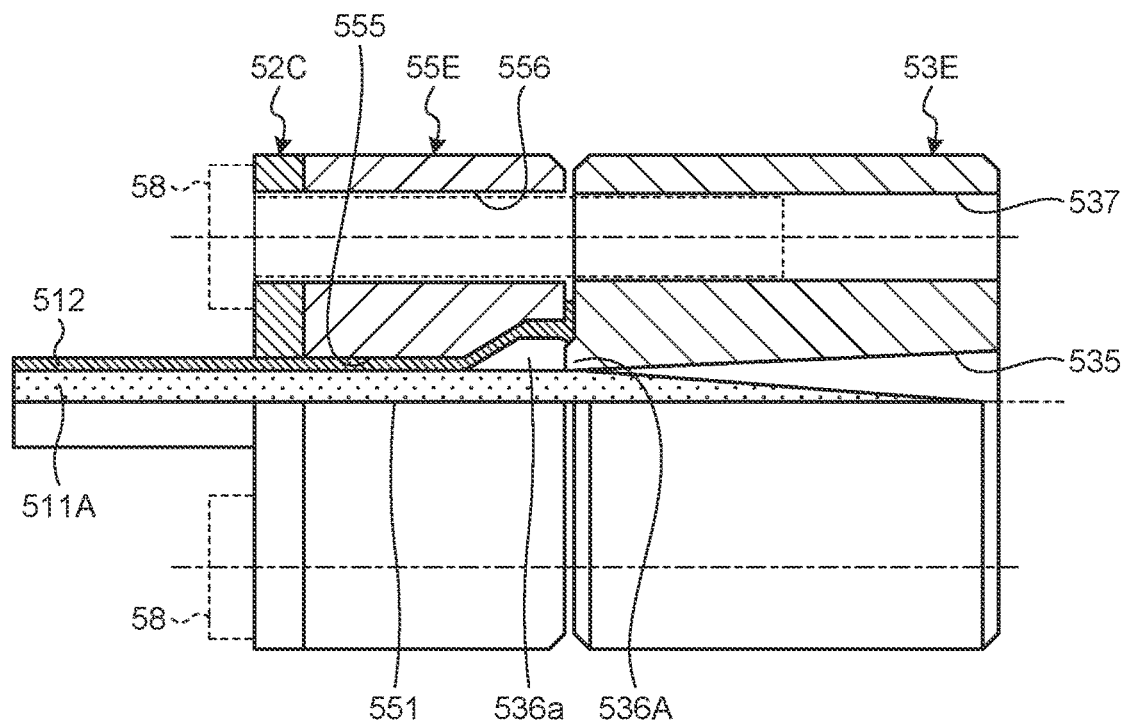
FIG. 33 is a partial sectional view illustrating a waveguide connecting structure according to a modified example of the fifth embodiment of the disclosure.
Figure 34:
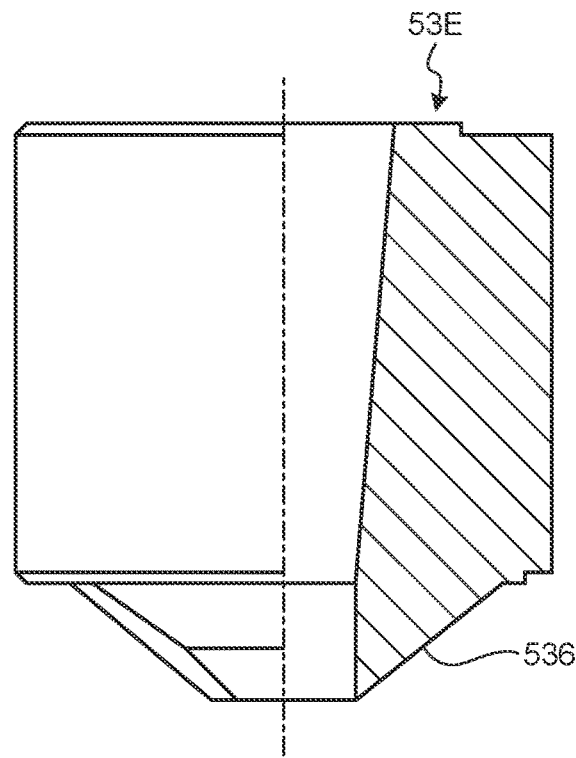
FIG. 34 is a partial sectional view illustrating a three-dimensional body according to the modified example of the fifth embodiment of the disclosure.
Figure 35:
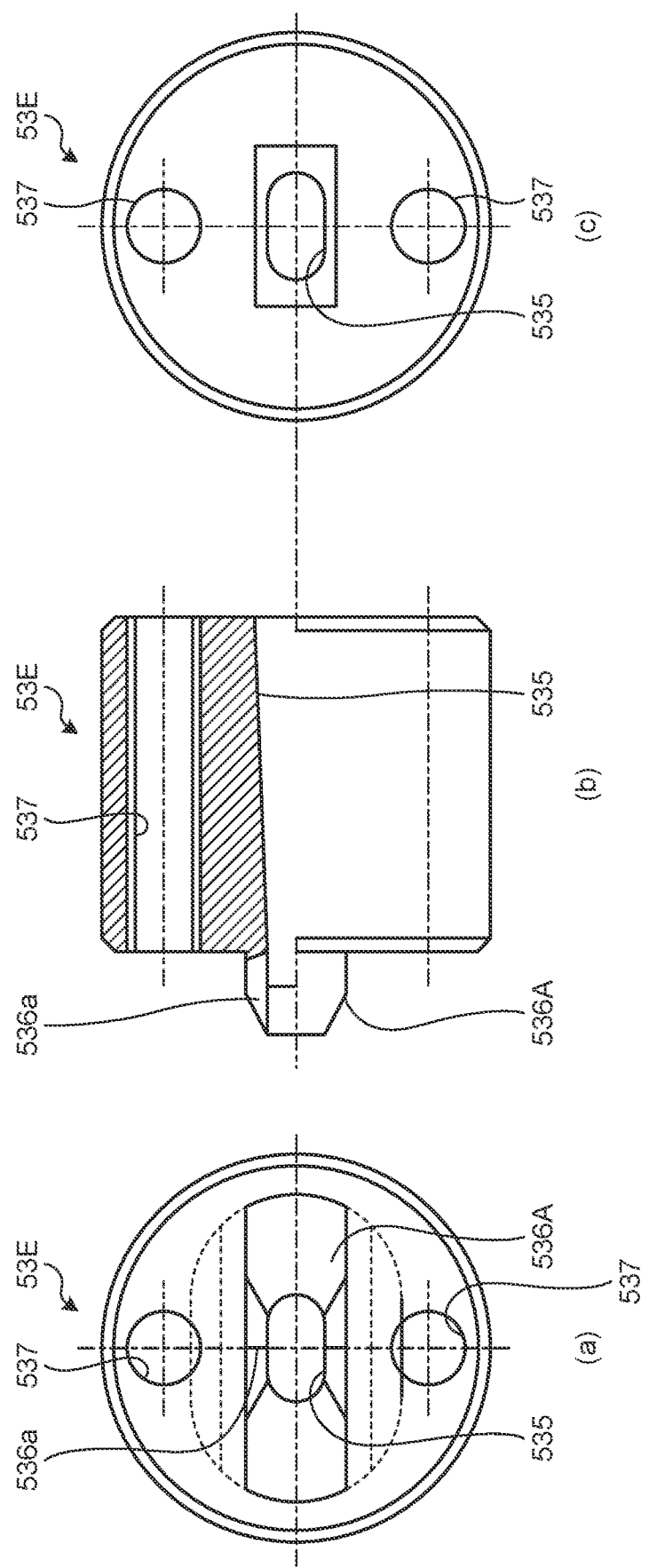
FIGS. 35(a), 35(b), and 35(c) are plan views for explaining a configuration of a fixing body and the three-dimensional body at a connection of a waveguide.

Next, a modified example of the fifth embodiment of the disclosure will be described by reference to FIG. 33 and FIG. 37. FIG. 33 is a partial sectional view illustrating a waveguide connecting structure according to the modified example of the fifth embodiment of the disclosure. FIG. 34 is a partial sectional view illustrating a three-dimensional body according to the modified example of the fifth embodiment of the disclosure. FIGS. 35(a), 35(b), and 35(c) are plan views for explaining a configuration of a fixing body and the three-dimensional body at a connection for the waveguide. An endoscope system according to this modified example has the same configuration as the fifth embodiment described above, except for the configuration of the three-dimensional body. This modified example includes a three-dimensional body 53E instead of the three-dimensional body 53D in the fifth embodiment described above. A configuration (the three-dimensional body 53E) different from that according to the fifth embodiment described above will be described below.

The three-dimensional body 53E is formed of a resin material that is moldable or a metallic material, such as brass. The three-dimensional body 53E includes the insertion hole 535 formed therein, the insertion hole 535 being where the dielectric body 511A is inserted. Furthermore, a sharp portion 536A is provided at an end of the three-dimensional body 53E, the end being an end that comes into contact with the fixing body 52C. Faces of the three-dimensional body 53E are electrically conductive, the faces including at least an inner surface of the insertion hole 535 and being faces that come into contact with the dielectric body 511A and the external conductor 512.

The fixing body 52C and the three-dimensional body 53E are fastened to each other with the screw 58, for example.

The sharp portion 536A includes the above described extended portion 538 and base portion 539, and is formed of a long diameter portion and a short diameter portion. The sharp portion 536 includes a notched portion 536a. The notched portion 536a is a slit that penetrates the sharp portion 536 along a thickness direction of the sharp portion 536, that is, from the inside to the outside of the sharp portion 536. The notched portion 536a divides the sharp portion 536 in the thickness direction, the sharp portion 536 being positioned around the insertion hole 535. The notched portion 536a is arranged on a center line of a long diameter of the sharp portion 536A. The notched portion 536a may be formed so as to leave a part of the thickness of the sharp portion 536, the part being near the base portion 539.

Figure 36:
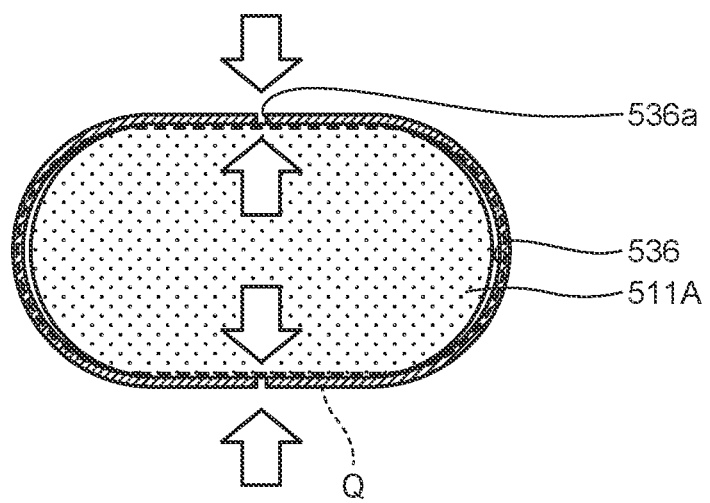
FIG. 36 is a first diagram illustrating a state of the waveguide when an elastic body is pressed against the waveguide.
Figure 37:
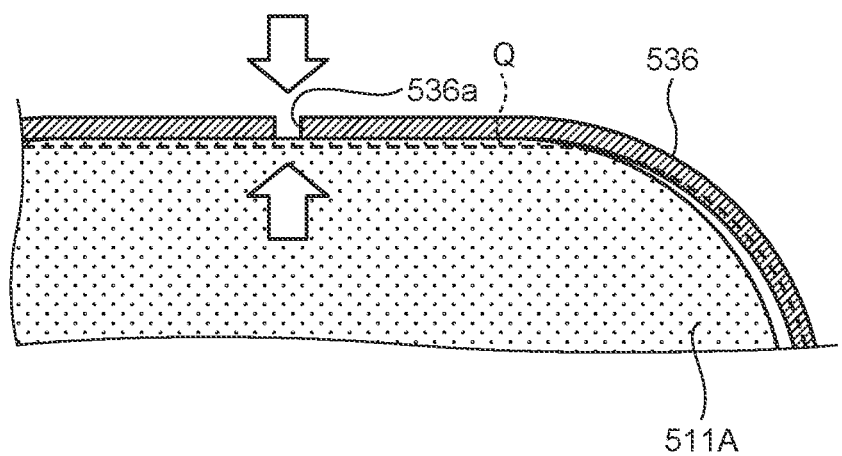
FIG. 37 is a second diagram illustrating the state of the waveguide when the elastic body is pressed against the waveguide.

FIG. 36 and FIG. 37 are diagrams illustrating a state of the waveguide when an elastic body is pressed against the waveguide. When the waveguide has been assembled, pressing force from the elastic body 55E and pressing force from the dielectric body 511A are applied to an opening portion of the three-dimensional body 53E, the opening portion being around the sharp portion 536A. Because the opening portion includes the notched portion 536a, the opening portion is easily deformed, and the shape of the opening is deformed by the above mentioned pressing force to follow the shape of the waveguide's core member (the dielectric body 511A) and the opening portion thus closely contacts the dielectric body 511A. The close contact of the shape of the opening, that is, the sharp portion 536A, with the dielectric body 511A enables loss (reflection) at the connection to be reduced. Furthermore, in the above described fifth embodiment, if the dielectric body 511A is slightly thicker than the dimension of the opening of the insertion hole 535, for example, the dielectric body 511A is unable to be inserted in the opening of the insertion hole 535, but in this modified example, because of the presence of the notched portion 536a, even if the cross-sectional dimension of the dielectric body 511A is slightly larger than that of the opening of the insertion hole 535, the sharp portion 536A is deformed, the dielectric body 511A is able to be inserted in the insertion hole 535, and the sharp portion 536A is able to be pressed against the dielectric body 511A to follow the shape of the dielectric body 511A.

Figure 38:
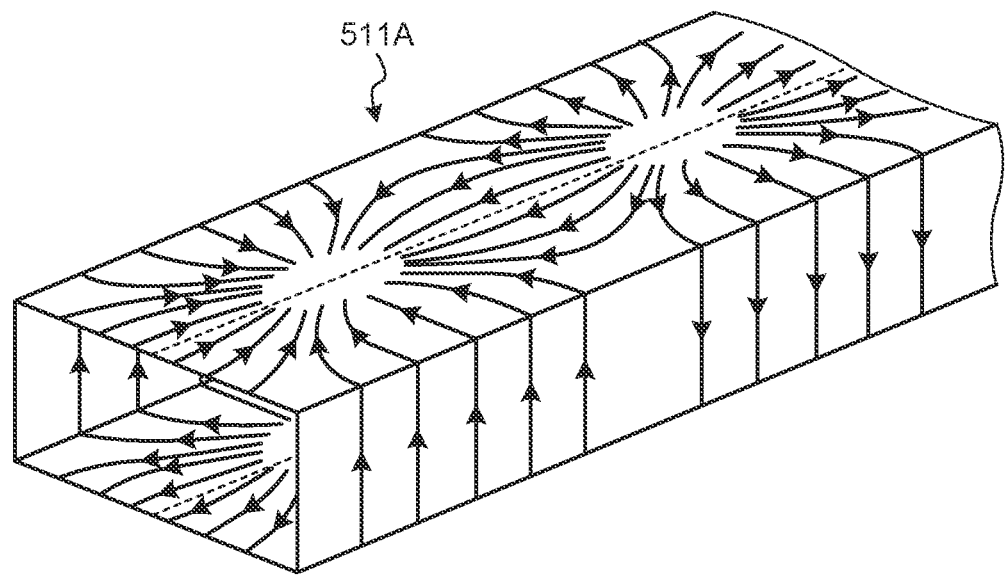
FIG. 38 is a diagram for explanation of directions of electric currents flowing in the waveguide.

The notched portion 536a is arranged on the center line of the long diameter because electric current flowing in the waveguide 51A does not flow across the center line of the long diameter portion in the TE10 mode that is the basic mode for the waveguide 51A. FIG. 38 is a diagram for explanation of directions of electric currents flowing in the waveguide. For the explanation, FIG. 38 is a diagram of a part of the dielectric body 511A, the part having been cut out from the dielectric body 511A, in a rectangular parallelepiped. Arrows in FIG. 38 indicate directions of electric currents flowing on wall surfaces in the waveguide 51A in the TE10 mode. For this waveguide 51A, even if the notched portion 536a is formed on the center line (a broken line in FIG. 38) of the long diameter portion, the electric currents will not be blocked, as evident from FIG. 38. That is, the modified example utilizes the physical property that providing the notched portion 536a on the center line of the long diameter portion does not lead to loss of radio waves conveyed inside the waveguide 51A.

In this modified example also, the elastic body 55E causes the external conductor 512 to closely contact the dielectric body 511A and the three-dimensional body 53E by respectively pressing the external conductor 512 interposed between the fixing body 52C and the dielectric body 511A and between the fixing body 52C and the three-dimensional body 53E.

Furthermore, in this modified example, forming the notched portion 536a in the sharp portion 536A of the three-dimensional body 53E enables the dielectric body 511A to be inserted in the insertion hole 535 even if the thickness of the dielectric body 511A is slightly larger than the size of the opening of the insertion hole 535.

The above described modified example also has effects similar to the above described effects of the fifth embodiment.

Sixth Embodiment

Figure 40:
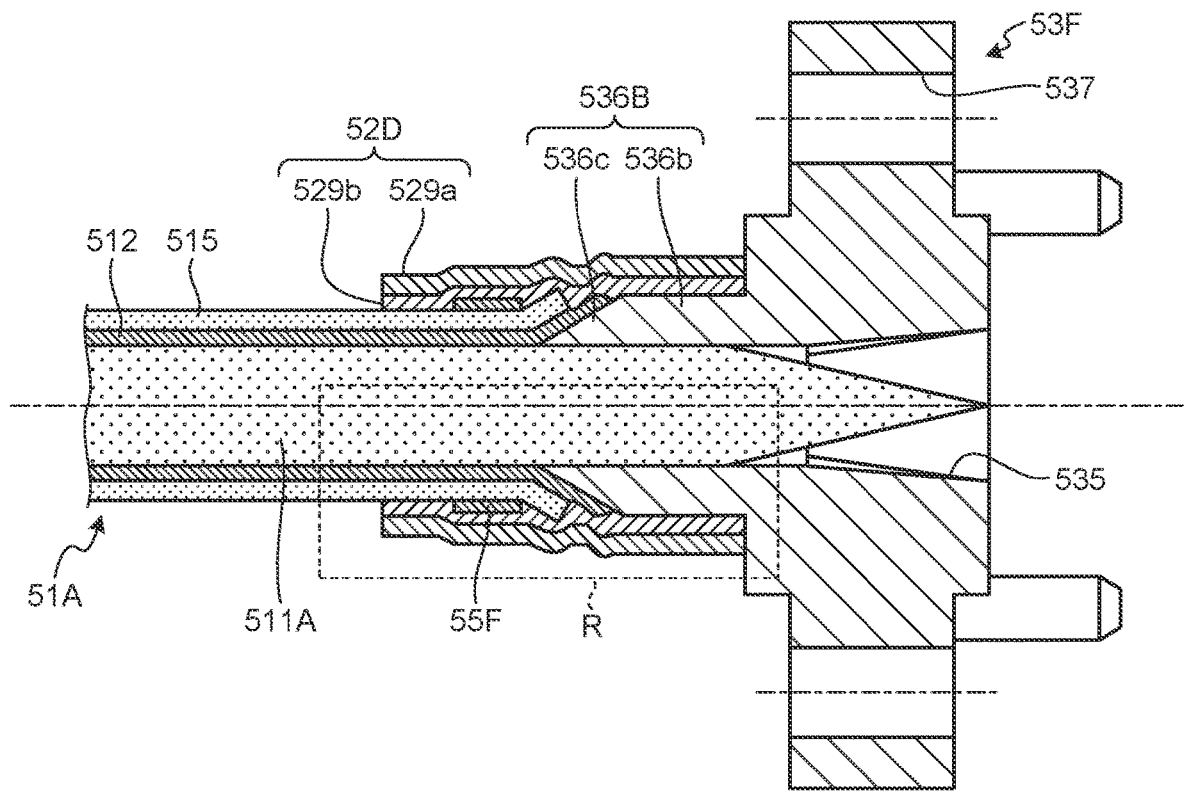
FIG. 40 is a sectional view illustrating a waveguide connecting structure according to a sixth embodiment of the disclosure.
Figure 41:
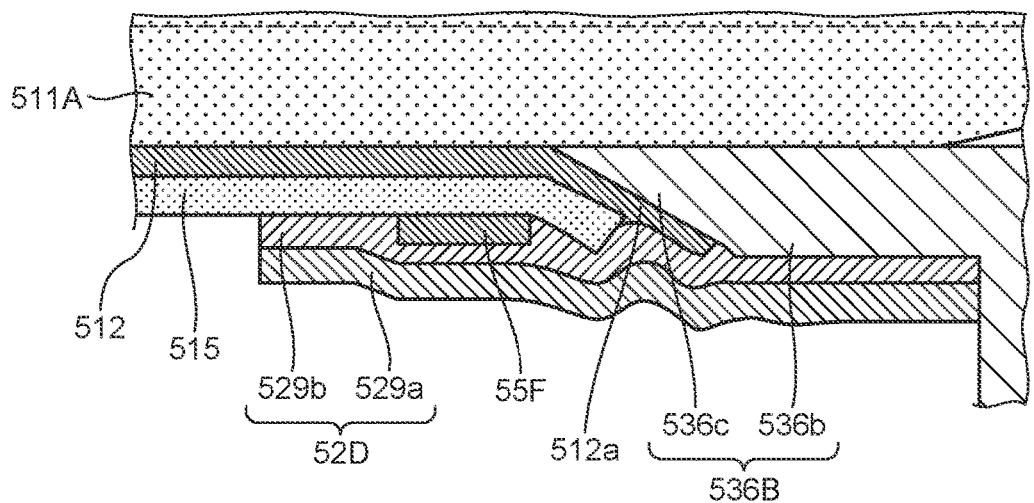
FIG. 41 is an enlarged view of a region R illustrated in FIG. 40.
Figure 42:
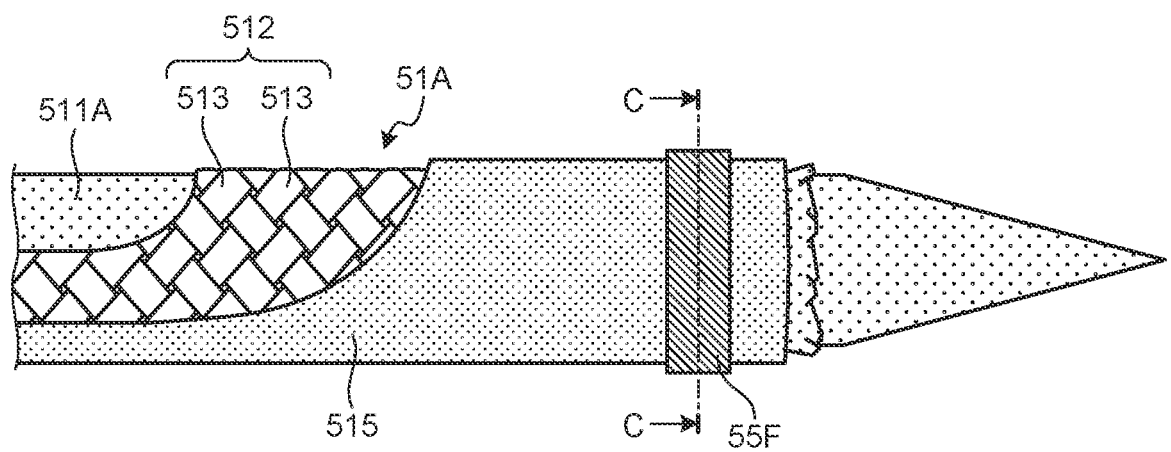
FIG. 42 is a diagram illustrating a configuration of a waveguide according to the sixth embodiment of the disclosure, the waveguide being a waveguide before installation in a three-dimensional body.
Figure 43:
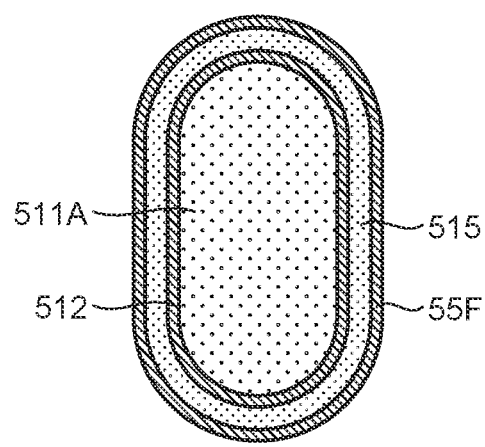
FIG. 43 is a sectional view taken upon a line C-C illustrated in FIG. 42.

Next, a sixth embodiment of the disclosure will be described by reference to FIG. 40 to FIG. 45. FIG. 40 is a sectional view illustrating a waveguide connecting structure according to the sixth embodiment of the disclosure. FIG. 41 is an enlarged view of a region R illustrated in FIG. 40. FIG. 42 is a diagram illustrating a configuration of a waveguide according to the sixth embodiment of the disclosure, the waveguide being a waveguide before installation in a three-dimensional body. FIG. 43 is a sectional view taken upon a line C-C illustrated in FIG. 42. An endoscope system according to the sixth embodiment has a configuration that is the same as that of the endoscope system 1 described above, except for the waveguide connecting structure. Any component different from that according to the first or third embodiment described above will be described below. For example, the fixing body needed for the connection in the third embodiment needs to be high in dimensional accuracy. Each component also needs to be a dedicated component tailored to the thickness of the waveguide. In contrast, the structure provided according to the sixth embodiment does not require high dimensional accuracy in a fixing body of the structure and is uncomplicated and inexpensive.

In the sixth embodiment, a three-dimensional body 53F is attached to a waveguide 51A. That is, the waveguide 51A is connected to another body (including another waveguide) via the three-dimensional body 53F.

The three-dimensional body 53F is formed of a resin material that is moldable or a metallic material, such as brass. An insertion hole 535 where a dielectric body 511A is inserted, and a screw hole 537 are formed in the three-dimensional body 53F. The insertion hole 535 forms a tapered space extending in an oblate hole shape and providing an opening that becomes larger with increasing distance from an end of the opening, the end being an end from which the dielectric body 511A is inserted into the opening.

Furthermore, a cylindrical portion 536B is provided in the three-dimensional body 53F at an end of the three-dimensional body 53F, the end being an end from which the dielectric body 511A is inserted into the three-dimensional body 53F. The cylindrical portion 536B is provided on the periphery of the insertion hole 535, the periphery including the position at which the insertion hole 535 is formed, and the cylindrical portion 536B protrudes in a direction parallel to a penetrating direction of the insertion hole 535. The cylindrical portion 536B includes a main body portion 536*b* extending in a hollow cylindrical shape and a sharp portion 536*c* that is annular and provided at an end of the main body portion 536*b*, the end being opposite to an opposite end of the main body portion 536*b*, the opposite end being closer to a main body of the three-dimensional body 53F. The sharp portion 536*c* has a section with a distal end forming an acute angle, the section being cut along a plane parallel to the penetrating direction of the insertion hole 535, the distal end being an end portion of the section, the end portion being opposite to an opposite end of the section, the opposite end being closer to the main body portion 536*b*. This angle of the distal end of the sharp portion 536*c* is set at, for example, 45° or more and 60° or less. The sharp portion 536*c* is positioned in a space formed between a radially spreading portion of an external conductor 512 (a connection enlarging portion 512*a*) and the dielectric body 511A. Protruding faces of the sharp portion 536*c* serve as a connected surface that comes into contact with each of the connection enlarging portion 512*a* and the dielectric body 511A.

Furthermore, a protective tube 515 covering the outer periphery of the external conductor 512 is provided in the waveguide 51A (see FIG. 42 and FIG. 43). A ring 55F is attached to a portion of the protective tube 515, the portion being close to a distal end of the protective tube 515. This ring 55F fixes adjacent ones of the dielectric body 511A, the external conductor 512, and the protective tube 515 to closely contact each other. The ring 55F is arranged at a portion on the outer periphery of the protective tube 515, the portion being closer to a proximal end of protective tube 515 than the distal end of the cylindrical portion 536B is. This ring 55F is formed of hard resin, for example. The ring 55F has a function of preventing the external conductor 512 and the protective tube 515 from unnecessarily spreading when the dielectric body 511A is inserted into the insertion hole 535 of the three-dimensional body 53F. The ring 55F corresponds to an elastic body. Instead of the ring 55F, tape made of resin, for example, may be used to be wrapped around.

A distal end (on the right in FIG. 40) portion of the dielectric body 511A has been inserted in the insertion hole 535 provided in the three-dimensional body 53F. Distal end portions of the external conductor 512 and the protective tube 515 spread outward to cover a sloped end face of the cylindrical portion 536B.

A protective body 52D thus covers a region including the ring 55F and extending from an outer peripheral surface of the protective tube 515, the outer peripheral surface being close to the distal end of the protective tube 515, to an outer peripheral surface of the cylindrical portion 536B. The protective body 52D is formed of a resin layer 529*a* provided outside and an adhesive layer 529*b* provided inside and is a so-called two-layered heat shrinkable tube, which is shrunk by heat. The protective body 52D corresponds to a fixing body that fixes position of the waveguide 51A relatively to the three-dimensional body 53F.

In a case where spread of the external conductor 512 and the protective tube 515 is able to be stopped by covering with the protective tube 515 and heating after insertion of the dielectric body 511A into the insertion hole 535 of the three-dimensional body 53F, a configuration excluding the ring 55F may be adopted. In that case, the protective tube 515 has a function as an elastic body.

Figure 44:
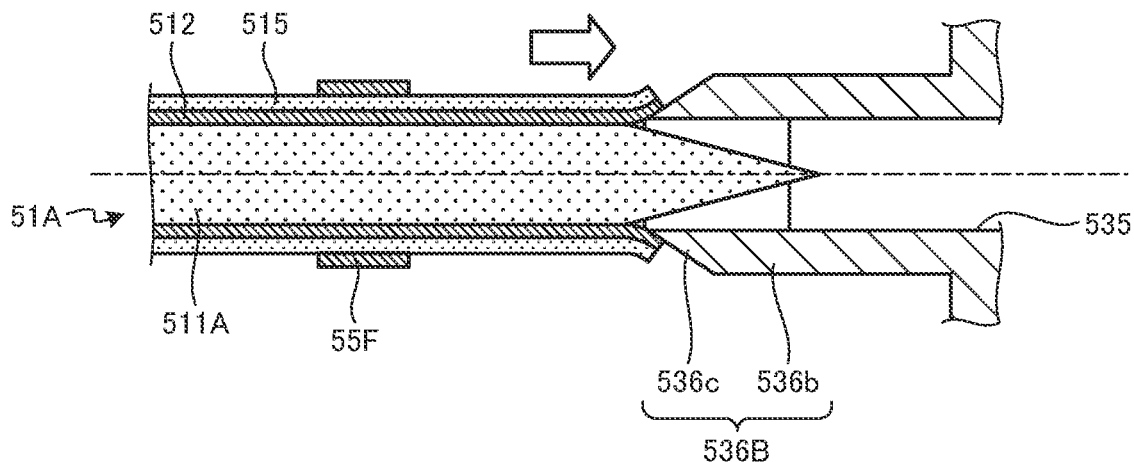
FIG. 44 is a first diagram for explanation of a method of assembling a waveguide connecting structure according to the sixth embodiment of the disclosure.
Figure 45:
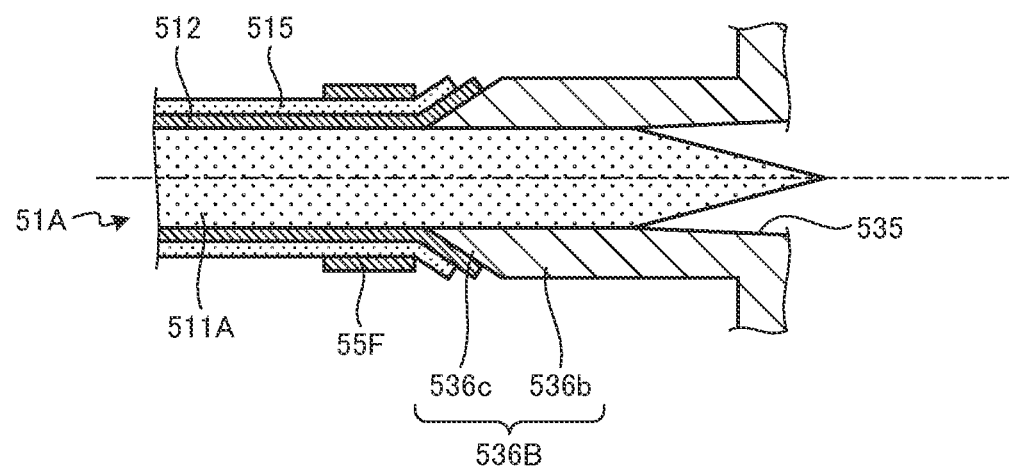
FIG. 45 is a second diagram for explanation of the method of assembling the waveguide connecting structure according to the sixth embodiment of the disclosure.

A method of assembling the waveguide connecting structure will be described next. FIG. 44 and FIG. 45 are diagrams for explanation of the method of assembling the waveguide connecting structure according to the sixth embodiment of the disclosure.

Firstly, the external conductor 512 and the protective tube 515 at a distal end portion of the waveguide 51A are removed. In a case where the exposed distal end of the dielectric body 511A is columnar, the distal end is cut. Thereafter, the ring 55F is attached at a preset position (see FIG. 44). This ring 55F is arranged at a position to face an end portion of the insertion hole 535 (an end portion of the sharp portion 536*c* herein) when the waveguide 51A has been inserted into the insertion hole 535 of the three-dimensional body 53F, the position corresponding, in a longitudinal direction, to a proximal end portion of the sharp portion 536*c*.

Subsequently, the dielectric body 511A is inserted into the insertion hole 535 (see FIG. 44). In this insertion, because the sharp portion 536c is acute-angled, the external conductor 512 is pushed to be spread outward over the cylindrical portion 536B while being pressed by the ring 55F. By this insertion being continued up to a position where the sharp portion 536c and the ring 55F face each other, the external conductor 512 is pressed against the end portion of the insertion hole 535 (the sharp portion 536c). By being pressed against the end portion of the insertion hole 535, position of the external conductor 512 is determined and electric continuity between the insertion hole 535 and the external conductor 512 is ensured.

Thereafter, the protective body 52D is placed to cover the region including the ring 55F and extending from the outer peripheral surface of the protective tube 515, the outer peripheral surface being close to the distal end of the protective tube 515, to the outer peripheral surface of the cylindrical portion 536B, the protective body 52D is then heated to be shrunk, and the protective body 52D is thereby caused to closely contact the protective tube 515 and the cylindrical portion 536B. In that process, the protective body 52D is adhered to the protective tube 515 and the cylindrical portion 536B by the adhesive layer 529b. The waveguide connecting structure illustrated in FIG. 40 is obtained by this assembling method.

The sixth embodiment described above has a configuration in which an elastic body, the ring 55F, causes the external conductor 512 to closely contact the dielectric body 511A and also causes the external conductor 512 to closely contact the sharp portion 536c of the three-dimensional body 53F. The sixth embodiment thus enables stable elimination or minimization of loss of radio waves in connecting a waveguide to another member, the waveguide including an external conductor having a braided structure.

Modified Example of Sixth Embodiment

Figure 46:
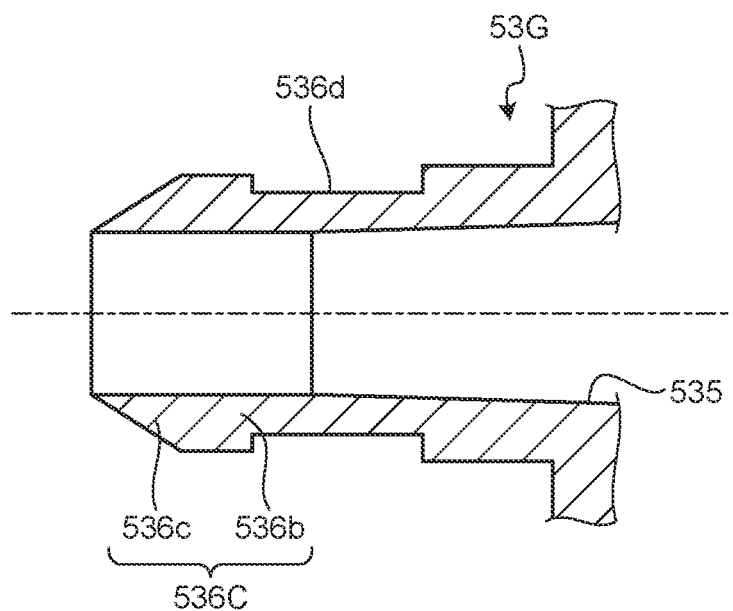
FIG. 46 is a sectional view illustrating a configuration of main parts of a three-dimensional body according to a modified example of the sixth embodiment of the disclosure.

Next, a modified example of the sixth embodiment of the disclosure will be described by reference to FIG. 46. FIG. 46 is a sectional view illustrating a configuration of main parts of a three-dimensional body according to the modified example of the sixth embodiment of the disclosure. An endoscope system according to this modified example has the same configuration as the sixth embodiment described above, except for the configuration of the three-dimensional body. This modified example includes a three-dimensional body 53G instead of the three-dimensional body 53F of the sixth embodiment described above. Any component (the three-dimensional body 53G) different from that according to the sixth embodiment described above will be described below.

The three-dimensional body 53G is formed of a resin material that is moldable or a metallic material, such as brass. The three-dimensional body 53G has an insertion hole 535 formed therein, the insertion hole 535 being where a dielectric body 511A is inserted. Furthermore, a cylindrical portion 536C is provided in the three-dimensional body 53G at an end of the three-dimensional body 53G, the end being an end from which the dielectric body 511A is inserted into the three-dimensional body 53G. The cylindrical portion 536C is provided around the opening of the insertion hole 535 and protrudes in a direction parallel to a penetrating direction of the insertion hole 535. The cylindrical portion 536C includes a main body portion 536b extending in a hollow cylindrical shape and a sharp portion 536c provided at an end of the main body portion 536b, the end being opposite to an opposite end of the main body portion 536b, the opposite end being closer to a main body of the three-dimensional body 53G. The cylindrical portion 536C has an engaging groove 536d formed therein. The engaging groove 536d is a recess formed on a part of a side surface of the main body portion 536b. By having an external conductor 512 and a protective tube 515 that are engaged with the engaging groove 536d and string, for example, wound around the protective tube 515, a waveguide 51A is able to be prevented from coming off the three-dimensional body 53G. Furthermore, by adhesion of the wound string to the protective tube 515 with an adhesive, the waveguide 51A and the three-dimensional body 53G are able to be fixed to each other even more infallibly.

Seventh Embodiment

Figure 47:
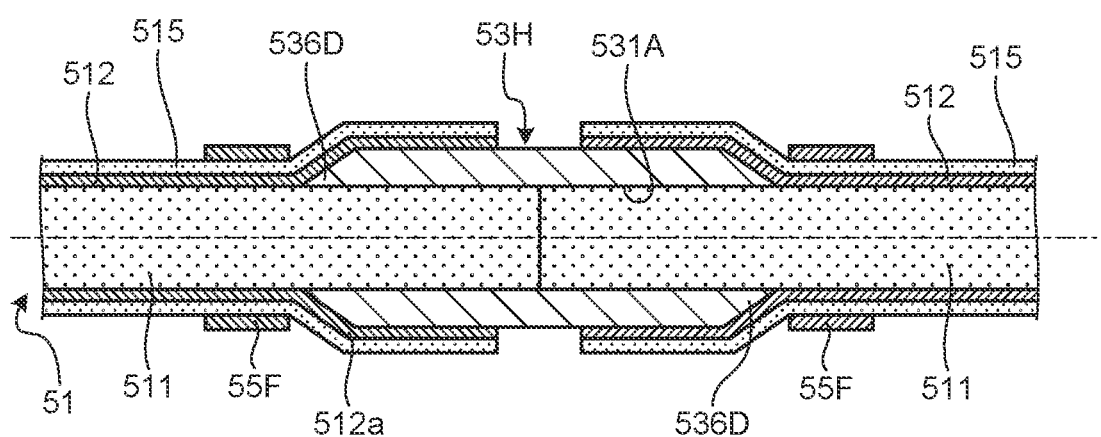
FIG. 47 is a sectional view illustrating a waveguide connecting structure according to a seventh embodiment of the disclosure.

Next, a seventh embodiment of the disclosure will be described by reference to FIG. 47 to FIG. 49. FIG. 47 is a sectional view illustrating a waveguide connecting structure according to the seventh embodiment of the disclosure. An endoscope system according to the seventh embodiment has a configuration that is the same as that of the endoscope system 1 described above, except for the waveguide connecting structure. Any component different from that of the above described first embodiment will be described below.

In the seventh embodiment, a three-dimensional body 53H is attached to waveguides 51. That is, two waveguides 51 are connected to each other via the three-dimensional body 53H.

The three-dimensional body 53H is formed of a resin material that is moldable or a metallic material, such as brass. The three-dimensional body 53H is a cylindrical body. Both end portions of the three-dimensional body 53H are tapered. The three-dimensional body 53H has an insertion hole 531A formed therein, the insertion hole 531A being where dielectric bodies 511 are inserted. The insertion hole 531A is a through hole extending in an oblate hole shape.

Furthermore, the three-dimensional body 53H includes a sharp portion 536D at each of the end portions of the three-dimensional body 53H. The sharp portions 536D each have a section with a distal end forming an acute angle, the section being taken upon a plane parallel to a penetrating direction of the insertion hole 531A. This angle at the distal end of the sharp portion 536D is set at, for example, 45° or more and 60° or less. The sharp portion 536D is positioned in a space formed between a radially spreading portion of an external conductor 512 (a connection enlarging portion 512a) and the dielectric body 511. Protruding faces of the sharp portion 536D serve as a connected surface that comes into contact with the connection enlarging portion 512a and the dielectric body 511.

Furthermore, a protective tube 515 covering the outer periphery of the external conductor 512 is provided in the waveguide 51. A ring 55F is attached to a portion of the protective tube 515, the portion being close to a distal end of the protective tube 515. This ring 55F fixes adjacent ones of the dielectric body 511, the external conductor 512, and the protective tube 515 to closely contact each other. The ring 55F is arranged at a portion on the outer periphery of the protective tube 515, the portion being closer to a proximal end of protective tube 515 than the distal end of the sharp portion 536D is. The ring 55F has a function of preventing the external conductor 512 and the protective tube 515 from unnecessarily spreading when the dielectric body 511 is inserted into the insertion hole 531A of the three-dimensional body 53H.

A distal end (on the right in FIG. 47) portion of the dielectric body 511 is positioned at a central portion of the insertion hole 531A provided in the three-dimensional body 53H. Distal end portions of the external conductor 512 and the protective tube 515 spread outward to cover a sloped end face of the sharp portion 536D.

A method of assembling the waveguide connecting structure will be described next. FIG. 48 and FIG. 49 are diagrams for explanation of the method of assembling the waveguide connecting structure according to the seventh embodiment of the disclosure.

Figure 48:
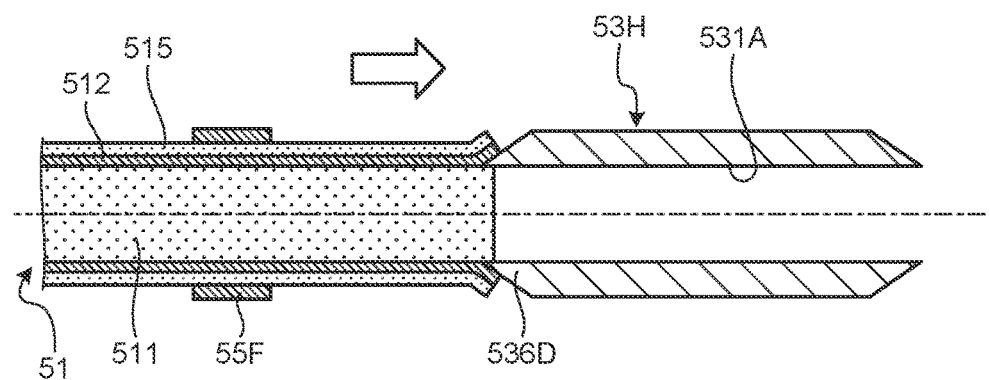
FIG. 48 is a first diagram for explanation of a method of assembling the waveguide connecting structure according to the seventh embodiment of the disclosure.

Firstly, the waveguide 51 with the ring 55F attached to the waveguide 51 is inserted into the insertion hole 531A (see FIG. 48). In this insertion, because the sharp portion 536D is acute-angled, the external conductor 512 is pushed to be spread outward over the sharp portion 536D while being pressed by the ring 55F. By this insertion being continued up to a position where the sharp portion 536D and the ring 55F face each other, the external conductor 512 is pressed against an end portion of the insertion hole 531A (the sharp portion 536D). By being pressed against the end portion of the insertion hole 531A, position of the external conductor 512 is determined and electric continuity between the insertion hole 531A and the external conductor 512 is ensured.

Figure 49:
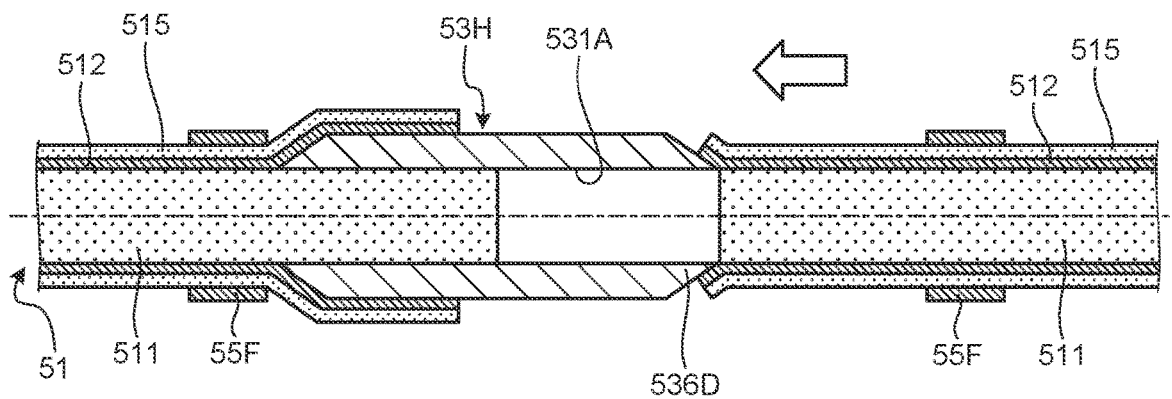
FIG. 49 is a second diagram for explanation of the method of assembling the waveguide connecting structure according to the seventh embodiment of the disclosure.

Similarly, the other waveguide 51 is inserted into the insertion hole 531A from the other end of the three-dimensional body 53H (see FIG. 49). By this insertion being performed until the dielectric body 511 comes into contact with the other dielectric body 511, the dielectric bodies 511 of the two waveguides 51 contact each other.

The connection between the waveguides 51 and/or a region including a portion of the protective tubes 515 of the waveguides 51 may be covered by a protective body. This protective body may be, for example, the protective body 52D described above.

The seventh embodiment described above has a configuration in which the ring 55F, at a connection between the external conductor 512 of the waveguide 51 and the three-dimensional body 53H, causes the external conductor 512 to closely contact the dielectric body 511 and causes the external conductor 512 (the connection enlarging portion 512a) to closely contact the three-dimensional body 53H. Because the external conductor 512 closely contacts the dielectric body 511 and the three-dimensional body 53, the seventh embodiment enables stable elimination or minimization of loss of radio waves in connecting a waveguide to another member, the waveguide including an external conductor having a braided structure.

Furthermore, as compared to the configuration according to the first embodiment, for example, the seventh embodiment enables streamlined connection between the waveguides 51. Therefore, adopting such a configuration for, for example, a connecting structure that does not require comparatively strong coupling (corresponding to mechanical coupling strength) enables connection between the waveguides 51 without the need for any elaborate component, like the fixing body 52 described above.

In the seventh embodiment, a part of a side surface of the three-dimensional body 53H may be formed into an engaging groove by being recessed. By having string, for example, that is wound around the protective tube 515, and the external conductor 512 and the protective tube 515 that are engaged with the engaging groove, the waveguide 51 is able to be prevented from coming off the three-dimensional body 53H. Furthermore, by adhesion of the wound string to the protective tube 515 with an adhesive, the waveguide 51 and the three-dimensional body 53H are able to be fixed to each other even more infallibly.

Modes for carrying out the disclosure have been described above, but the disclosure should not be limited to the embodiments described above only. The disclosure may include various embodiments not described herein.

The waveguide connecting structures according to the first to fifth embodiments have been described above by referring to flexible waveguides having flexibility as an example, but the waveguides are not necessarily those having flexibility, and may be other kinds of waveguides, such as semi-flexible waveguides or rigid waveguides, as long as they have braided external conductors.

Furthermore, with respect to the third to fifth embodiments, the connecting structure for smooth change in the thickness of a waveguide for connection to a hollow hole portion (a waveguide) has been described as an example, but without being limited to this example, these embodiments are widely applicable to any connection between a waveguide and a member to be connected to the waveguide.

Figure 39:
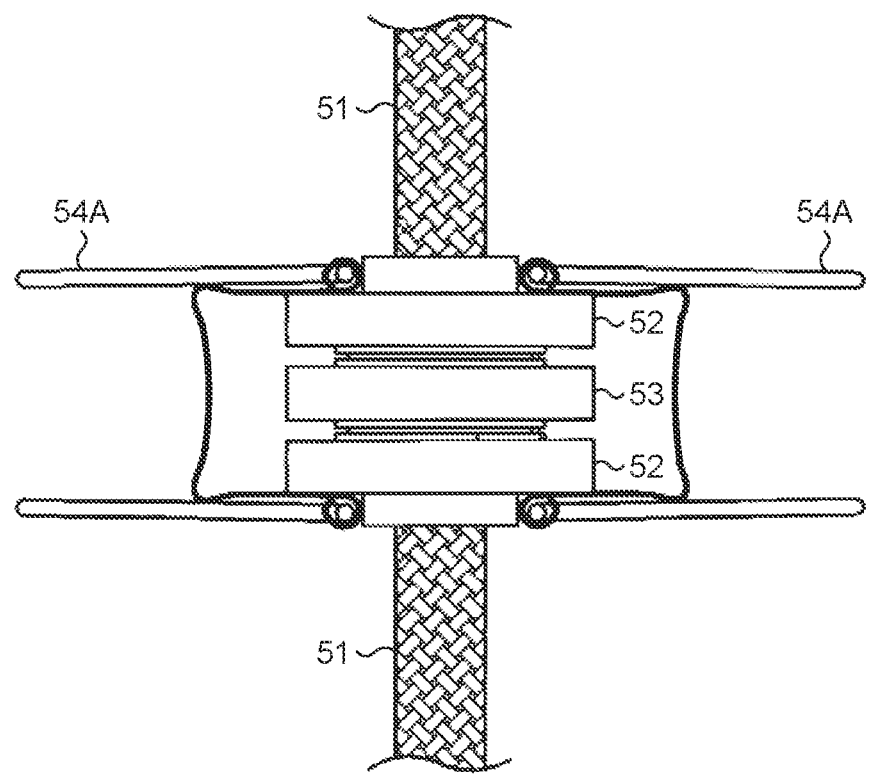
FIG. 39 is a diagram illustrating another example of a pressing aiding member.

Furthermore, although the first embodiment has been described by referring to grating clips as an example of the pressing aiding members 54, the pressing aiding members 54 are not necessarily these clips, and for example, a clip having another shape, a screw, an elastic body such as rubber, or an adhesive may be used to provide equivalent functions. FIG. 39 is a diagram illustrating another example of pressing aiding members. Pressing aiding members 54A illustrated in FIG. 39 are formed using double clips. These pressing aiding members 54A may be used to fix the fixing body 52 and the three-dimensional body 53 to each other.

A waveguide connecting structure, a waveguide connector, a waveguide unit, a mode converter, an imaging device, and an endoscope, according to the disclosure described above are useful for stably reducing loss of radio waves in connecting a waveguide to another member, the waveguide including an external conductor having a braided structure.

The disclosure has an effect of stably reducing loss of radio waves in connecting a waveguide to another member, the waveguide including an external conductor having a braided structure.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A waveguide connecting structure configured to connect a first waveguide to a second waveguide which is different from the first waveguide, or to connect the first waveguide to a transmitting and receiving device which is configured to transmit and receive radio waves, the waveguide connecting structure comprising:

an elastic body configured to cause an external conductor to closely contact a dielectric body, the external conductor and the dielectric body being included in the first waveguide which is configured to transmit the radio waves having a frequency of millimeter waves or higher, the external conductor covering an outer periphery of the dielectric body; and a three-dimensional body configured to hold the dielectric body of the first waveguide, and the second waveguide or the transmitting and receiving device, wherein the three-dimensional body has electric conductivity inside an insertion hole for holding the first waveguide, and wherein the external conductor of the first waveguide includes a radially spread portion where the external conductor has been radially spread away from the outer periphery of the dielectric body, the radially spread portion being where the first waveguide and the three-dimensional body are connected to each other.

2. The waveguide connecting structure according to claim 1, wherein the three-dimensional body includes a sharp portion that is in contact with each of the radially spread portion of the external conductor and the dielectric body.

3. The waveguide connecting structure according to claim 2, wherein the sharp portion forms an acute angle and is positioned in a space formed between the radially spread portion and the dielectric body.

4. The waveguide connecting structure according to claim 3, further comprising:
a fixing body configured to hold the elastic body, the external conductor being inserted through the fixing body; and
a holding body configured to hold the fixing body and the three-dimensional body closely to each other along a longitudinal direction of the dielectric body.

5. The waveguide connecting structure according to claim 4, wherein the elastic body has an elastic modulus lower than those of the dielectric body, the fixing body, and the three-dimensional body.

6. The waveguide connecting structure according to claim 5, wherein the elastic body has a Shore-A rubber hardness of 20 or more and 70 or less.

7. A waveguide unit, comprising:
the waveguide connecting structure according to claim 4, the fixing body being provided at each of both ends of the first waveguide.

8. The waveguide connecting structure according to claim 4, wherein the sharp portion is configured to be positioned between the elastic body and the dielectric body and protrudes toward the fixing body.

9. The waveguide connecting structure according to claim 8, wherein:
the three-dimensional body includes a holding surface that is in contact with the dielectric body to hold the dielectric body, and
the sharp portion is thinner at a first portion where a cross-sectional shape of the dielectric body has a large curvature radius, than at a second portion where the cross sectional shape of the dielectric body has a small curvature radius, the first portion and the second portion facing the sharp portion.

10. The waveguide connecting structure according to claim 9, wherein a clearance between the dielectric body and the external conductor and between the dielectric body and the holding surface of the three-dimensional body is $1/50$ or less of a wavelength.

11. The waveguide connecting structure according to claim 8, wherein the sharp portion includes a slit.

12. The waveguide connecting structure according to claim 3, wherein the elastic body is provided to cover the external conductor, and
the elastic body has a sheet shape or is tubular.

13. A waveguide connector, comprising:
two or more of waveguide connecting structures where each is the waveguide connecting structure according to claim 3.

14. The waveguide connecting structure according to claim 3, wherein the three-dimensional body is formed using a resin material that is moldable, and includes an electrically conductive surface layer formed on at least faces of the three-dimensional body, the faces being faces that are in contact with the dielectric body and the external conductor.

15. An imaging device, comprising:
the waveguide connecting structure according to claim 3;
an optical lens configured to condense light from outside;
an imaging element configured to photoelectrically convert the light condensed by the optical lens; and
an image processor configured to process a signal input from the imaging element via the waveguide.

16. An endoscope, comprising:
the imaging device according to claim 15.

17. A mode converter, comprising:
the waveguide connecting structure according to claim 3, wherein the waveguide connecting structure connects the first waveguide and the transmitting and receiving device to each other,
wherein the transmitting and receiving device includes an antenna for mode conversion between a mode for electromagnetic waves and a mode for electric signals.

18. A waveguide connecting structure configured to connect a first waveguide to a second waveguide which is different from the first waveguide, or to connect the first waveguide to a transmitting and receiving device which is configured to transmit and receive radio waves, the waveguide connecting structure comprising:
the first waveguide, which is configured to transmit the radio waves having a frequency of millimeter waves or higher, and which comprises a dielectric body and an external conductor, the external conductor covering an outer periphery of the dielectric body;
an elastic body configured to cause the external conductor to closely contact the dielectric body; and
a three-dimensional body configured to hold the dielectric body of the first waveguide, and the second waveguide or the transmitting and receiving device,
wherein the three-dimensional body has electric conductivity inside an insertion hole for holding the first waveguide, and
wherein the external conductor of the first waveguide includes a radially spread portion where the external conductor has been radially spread away from the outer periphery of the dielectric body, the radially spread portion being where the first waveguide and the three-dimensional body are connected to each other.

* * * * *